US011713234B2

(12) United States Patent
Chang et al.

(10) Patent No.: US 11,713,234 B2
(45) Date of Patent: Aug. 1, 2023

(54) BEVERAGE DISPENSER NETWORK AND PROFILE MANAGEMENT

(71) Applicant: THE COCA-COLA COMPANY, Atlanta, GA (US)

(72) Inventors: Franchot Chang, Marietta, GA (US); Joshua Casey Schwarber, Decatur, GA (US); Augusto Elias, Atlanta, GA (US); Jed Lawton Coxon, Suwanee, GA (US); Martin Kilcoyne, Derby (GB)

(73) Assignee: THE COCA-COLA COMPANY, Atlanta, GA (US)

( * ) Notice: Subject to any disclaimer, the term of this patent is extended or adjusted under 35 U.S.C. 154(b) by 0 days.

(21) Appl. No.: 17/257,958

(22) PCT Filed: Jul. 5, 2019

(86) PCT No.: PCT/US2019/040714
§ 371 (c)(1),
(2) Date: Jan. 5, 2021

(87) PCT Pub. No.: WO2020/010322
PCT Pub. Date: Jan. 9, 2020

(65) Prior Publication Data
US 2021/0179412 A1 Jun. 17, 2021

Related U.S. Application Data
(60) Provisional application No. 62/694,685, filed on Jul. 6, 2018.

(51) Int. Cl.
*B67D 1/08* (2006.01)
*H04L 29/08* (2006.01)
(Continued)

(52) U.S. Cl.
CPC ......... *B67D 1/0888* (2013.01); *B67D 1/0034* (2013.01); *G07F 9/002* (2020.05);
(Continued)

(58) Field of Classification Search
CPC ... B67D 1/0888; B67D 1/0034; H04L 67/306; H04L 67/12; G07F 9/002; G07F 13/065; G16H 20/60
See application file for complete search history.

(56) References Cited

U.S. PATENT DOCUMENTS 7,295,889 B2 * 11/2007 Lahteenmaki ......... G16H 20/60
700/239
7,578,415 B2 8/2009 Ziesel et al.
(Continued)

FOREIGN PATENT DOCUMENTS

CN 101395086 A 3/2009
CN 102712453 A 10/2012
(Continued)

OTHER PUBLICATIONS

English translation of Notice of Reasons for Rejection issued in JP Application No. 2020-508607, dated Jun. 17, 2022.
(Continued)

*Primary Examiner* — Michael Collins
(74) *Attorney, Agent, or Firm* — Meunier Carlin & Curfman LLC

(57) ABSTRACT

Athletes in an athletic organization are provided access to a network of beverage dispensers associated with the organization. User profiles for each of the athletes are actively synchronized on the beverage dispensers within the network in response to changes to any of the user profiles. The user profiles are centrally maintained on a profile database and each profile includes performance parameters and personal parameters. Different users are given different levels of
(Continued)

access to the user profiles. Each athlete is given access to view their entire profile and make modifications to personal parameters in their profile. Likewise, trainers or other training staff of the athletic organization are given access to view personal parameters of athlete's profiles and access to make modifications to performance parameters. Upon receiving a selection of an athlete's profile, a dispenser in the network is configured according to the personal and performance parameters stored in their profile.

9 Claims, 9 Drawing Sheets

(51) Int. Cl.
  *B67D 1/00* (2006.01)
  *H04L 67/12* (2022.01)
  *H04L 67/306* (2022.01)
  *G07F 9/00* (2006.01)
  *G07F 13/06* (2006.01)
  *G16H 20/60* (2018.01)

(52) U.S. Cl.
  CPC ........... *G07F 13/065* (2013.01); *G16H 20/60* (2018.01); *H04L 67/12* (2013.01); *H04L 67/306* (2013.01)

(56) References Cited

U.S. PATENT DOCUMENTS

| | | | |
|---|---|---|---|
| 7,866,509 B2 | 1/2011 | Ziesel | |
| 7,912,579 B2 * | 3/2011 | Stettes | G07F 13/065 700/231 |
| 8,333,224 B2 | 12/2012 | Sheehy et al. | |
| 8,560,334 B2 * | 10/2013 | Lahteenmaki | G16H 40/67 705/2 |
| 9,173,517 B2 * | 11/2015 | Bulgin | A47J 31/402 |
| 9,394,154 B2 | 7/2016 | Connerat et al. | |
| 10,399,838 B2 | 9/2019 | Green | |
| 10,631,558 B2 | 4/2020 | White et al. | |
| 10,800,643 B2 | 10/2020 | Gatipon et al. | |
| 11,017,768 B2 * | 5/2021 | Crawford | G10L 15/30 |
| 11,312,608 B2 * | 4/2022 | Lane | B67D 1/0037 |
| 2004/0026452 A1 * | 2/2004 | Santiago | G07F 13/065 62/392 |
| 2005/0048461 A1 * | 3/2005 | Lahteenmaki | G06Q 10/10 435/3 |
| 2005/0133420 A1 | 6/2005 | Rinker et al. | |
| 2007/0073557 A1 | 3/2007 | Abramson | |
| 2008/0206429 A1 * | 8/2008 | Guerrero | B67D 1/0895 222/129.4 |
| 2009/0032609 A1 | 2/2009 | Ziesel | |
| 2010/0273224 A1 | 10/2010 | Joachim et al. | |
| 2011/0121032 A1 | 5/2011 | Deo et al. | |
| 2013/0282169 A1 | 10/2013 | Moore et al. | |
| 2014/0272853 A1 | 9/2014 | Sakai et al. | |
| 2014/0337795 A1 | 11/2014 | Deo et al. | |
| 2015/0082243 A1 | 3/2015 | Taylor et al. | |
| 2016/0090288 A1 | 3/2016 | Givens et al. | |
| 2016/0157749 A1 | 6/2016 | Bohorquez et al. | |
| 2016/0255991 A1 | 9/2016 | Givens, Jr. et al. | |
| 2017/0022043 A1 | 1/2017 | Newman et al. | |
| 2017/0225936 A1 | 8/2017 | Jersey et al. | |
| 2019/0308866 A1 | 10/2019 | Sawhney et al. | |
| 2020/0122994 A1 * | 4/2020 | Cimatti | B67D 1/0034 |

FOREIGN PATENT DOCUMENTS

| | | |
|---|---|---|
| CN | 103003189 A | 3/2013 |
| JP | 2006181507 A | 7/2006 |
| JP | 2010539911 A | 12/2010 |
| JP | 4881472 B1 | 2/2012 |
| JP | 2014176439 A | 9/2014 |
| JP | 2015520079 A | 7/2015 |
| JP | 2016099768 A | 5/2016 |
| KR | 10-2007-0026572 A | 3/2007 |
| KR | 10-2016-0138166 A | 12/2016 |
| WO | 32025608 A1 | 3/2002 |
| WO | 2007136904 A2 | 11/2007 |
| WO | 2011066444 A1 | 6/2011 |
| WO | 2011139550 A1 | 11/2011 |
| WO | 2015167846 | 11/2015 |
| WO | 2016058919 A1 | 4/2016 |
| WO | 2016141322 | 9/2016 |
| WO | 2017058794 | 4/2017 |
| WO | 2017192871 A1 | 11/2017 |

OTHER PUBLICATIONS

Office Action issued by the Chinese National Intellectual Property Administration in Chinese Application No. 2018800593450 dated May 6, 2021. 11 pages including English translation.
International Search Report and Written Opinion for International Application No. PCT/US2019/040714 dated Oct. 25, 2019.
International Search Report and Written Opinion issued by the International Searching Authority (ISA/KR) in PCT Application No. PCT/IB2018/056183 dated Dec. 6, 2018. 11 pages.
Supplementary European Search Report for European Application No. 18847009 dated Apr. 8, 2021.
Office Action issued for U.S. Appl. No. 16/639,361, dated Oct. 28, 2020.
Notice of Allowance issued for U.S. Appl. No. 16/639,361, dated Apr. 14, 2021.

* cited by examiner

BEVERAGE DISPENSER NETWORK AND PROFILE MANAGEMENT

This application is a national stage application filed under 35 U.S.C. § 371 of PCT/US2019/040714 on Jul. 5, 2019, which claims the benefit of U.S. Provisional Patent Application Ser. No. 62/694,685 filed Jul. 6, 2018, the disclosures of which are expressly incorporated herein by reference.

BACKGROUND

Traditional post-mix beverage dispensing systems generally mix streams of syrup, concentrate, sweetener, bonus flavors, other types of flavorings, and/or other ingredients with water or other types of diluents by flowing the syrup stream down the center of the nozzle with the water stream flowing around the outside. The syrup stream is directed downward with the water stream such that the streams mix as they fall into a consumer's cup. There is a desire for a beverage dispensing system as a whole to provide as many different types and flavors of beverages as may be possible in a footprint that may be as small as possible. Recent improvements in beverage dispensing technology have focused on the use of micro-ingredients. With micro-ingredients, the traditional beverage bases may be separated into their constituent parts at much higher dilution or reconstitution ratios.

This technology is enabled via cartridges containing the highly concentrated micro-ingredients. The micro-ingredients are mixed with sweeteners and still or sparkling water using precise metering and dosing technologies and dispensed through a nozzle that promotes in-air mixing so as to prevent carry-over. The technology includes a user input for a user to select a desired beverage, customize the beverage if desired, and pour the beverage at the dispenser. These beverages are made from precise recipes to ensure a great tasting beverage regardless of the customization.

Trainers and the like may monitor an athlete's biometric data and nutritional intake to promote peak performance. This data may include weight, hydration level, heart rate, water intake, carbohydrate intake, protein intake, supplement intake, sodium intake, blood pressure, expended and intended exertion, temperature, blood oxygen levels, and other metrics. Trainers thus may seek to tailor a given type of sports drink with a number of additives for a specific athlete or a specific type of athlete. Mixing such additives for a number of athletes, however, may be a time-consuming process, particularly during a game or on the practice field.

SUMMARY

According to a first aspect of the disclosure, a beverage dispenser network comprises a profile database configured to store a user profile. The user profile comprises a personal parameter for a beverage and a performance parameter for the beverage. The beverage dispenser network further comprises a server configured to receive an update to the user profile that changes the personal parameter or the performance parameter. The beverage dispenser network further comprises a plurality of beverage dispensers configured to receive the user profile with the changed personal or performance parameter from the server in response to the update.

In some implementations of the first aspect of the disclosure, the personal parameter is a flavor, flavor intensity level, level of sweetness, or other non-functional additive for a dispensed beverage.

In some implementations of the first aspect of the disclosure, the performance parameter is a vitamin, mineral, electrolyte, sodium, potassium, magnesium, calcium, protein, carbohydrate, medicine or other functional additive for a dispensed beverage.

In some implementations of the first aspect of the disclosure, the server is configured to permit an administrative user to provide the update to change the performance parameter of the user profile.

In some implementations of the first aspect of the disclosure, the server is further configured to permit an end user to provide the update to change the personal parameter of the user profile.

In some implementations of the first aspect of the disclosure, the server is further configured to deny the end user to provide the update to change the performance parameter of the user profile.

In some implementations of the first aspect of the disclosure, the administrative user is an athletic trainer and the end user is an athlete.

In some implementations of the first aspect of the disclosure, the beverage dispenser network further comprises an external display configured to show a report of a dispensing session completed on one of the plurality of beverage dispensers.

In some implementations of the first aspect of the disclosure, each of the plurality of beverage dispensers and the user profile are associated with a common customer number.

According to a second aspect of the disclosure, a beverage dispenser comprises a nozzle configured to dispense beverage ingredients of a beverage. The beverage dispenser comprises a user interface configured to receive a selection of a user profile from among a plurality of user profiles maintained by the beverage dispenser. Each of the plurality of user profiles comprising a personal parameter for a beverage and a performance parameter for the beverage. The beverage dispenser comprises a plurality of pumping devices, each configured to supply a beverage ingredient from an ingredient source to the nozzle. The beverage dispenser comprises a controller configured to receive an updated user profile, wherein the updated user profile comprises a changed personal or performance parameter for one of the plurality of user profiles.

In some implementations of the second aspect of the disclosure, the personal parameter is a flavor, flavor intensity level, level of sweetness, or other non-functional additive for a dispensed beverage.

In some implementations of the second aspect of the disclosure, the performance parameter is a vitamin, mineral, electrolyte, sodium, potassium, magnesium, calcium, protein, carbohydrate, medicine or other functional additive for a dispensed beverage.

In some implementations of the second aspect of the disclosure, the controller is further configured to generate a dispensing session message upon completion of a dispensing session.

In some implementations of the second aspect of the disclosure, the dispensing session message includes one or more of a user profile identifier associated with the dispensing session, identifiers of personal and performance parameters used to dispense a beverage in the dispensing session, an amount of the beverage, or an amount of one or more of the beverage ingredients dispensed in the dispensing session.

In some implementations of the second aspect of the disclosure, the controller is further configured to activate one or more of the plurality of pumping devices in response to the selected user profile based on the personal parameter and the performance parameter.

In some implementations of the second aspect of the disclosure, the controller is further configured to activate at least a different one of the plurality of pumping devices in response to the updated profile.

In a third aspect of the disclosure, a method of maintaining a beverage dispenser network comprises storing a user profile associated with a customer number in a profile database. The user profile comprises a personal parameter for a beverage and a performance parameter for the beverage. The method also comprises receiving a first update to the user profile from an end user, wherein the first update changes the personal parameter. The method also comprises receiving a second update to the user profile from an administrative user, wherein the second update changes the performance parameter. The method also comprises synchronizing the user profile across a plurality of beverage dispensers associated with the customer number in response to the first and second update.

In some implementations of the third aspect of the disclosure, the personal parameter is a flavor, flavor intensity level, level of sweetness, or other non-functional additive for a dispensed beverage.

In some implementations of the third aspect of the disclosure, the performance parameter is a vitamin, mineral, electrolyte, sodium, potassium, magnesium, calcium, protein, carbohydrate, medicine or other functional additive for a dispensed beverage.

In some implementations of the third aspect of the disclosure, the method further comprises receiving a third update to a second user profile from the administrative user, wherein the third update changes a second performance parameter of the second user profile.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
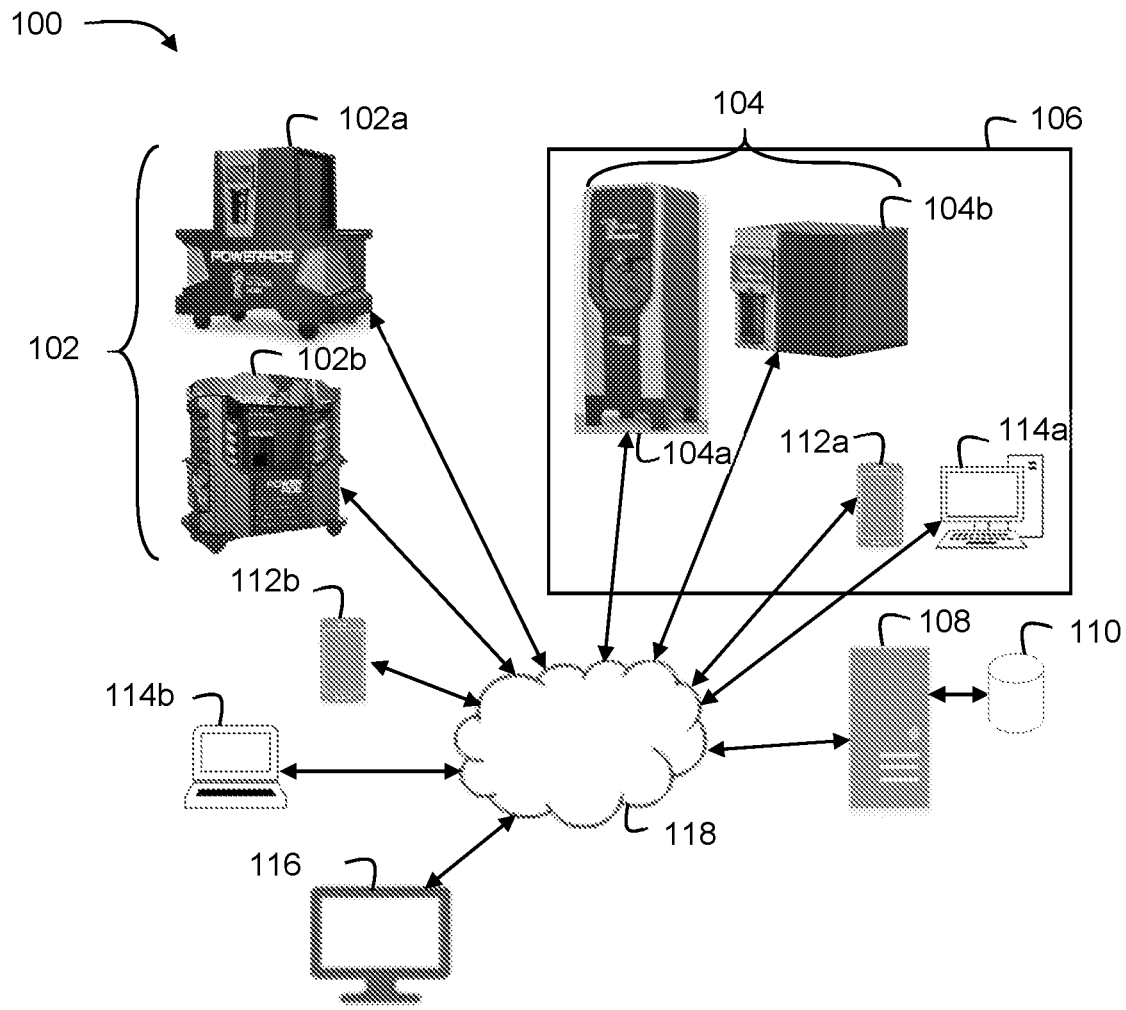
FIG. 1 illustrates an exemplary block diagram of a beverage dispenser network according to various embodiments of the disclosure.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A", "B", and/or "C" means "A", or "B", or "C", or "A and B", or "A and C", or "A and B and C".

A beverage dispenser may facilitate a personalized beverage dispensing operation with a consumer upon obtaining a user profile for the consumer. The user profile may include preferences such as favorite beverages or custom mixed beverages, each mixed beverage formed from a mixture of two or more standard beverages. Upon loading the consumer profiled, the beverage dispenser may present a customized menu of the consumer's favorites and mixes, for example. Other profile information and menu options may be available.

Beverage dispensers are typically installed in locations where they server tens or hundreds of consumers throughout a day and each dispenser serves a different set of consumers. It is generally not feasible to pre-load consumer profiles onto the dispensers due to uncertainty of which dispenser(s) will be used by a given consumer on a given day and memory limitations of dispensers to not be able to store all consumer profiles. Therefore, a given beverage dispenser typically does not obtain and load a particular consumer's profile until the consumer is near to or addressing (e.g., in front of) the beverage dispenser. For example, a consumer's profile may be delivered to a beverage dispenser upon an application on the consumer's mobile device reading a code that uniquely identifies the beverage dispenser, as described in commonly owned Pat. App. PCT/US2016/053961, "Dispenser Connectivity," filed Sep. 27, 2016, hereby incorporated by reference in its entirety for all purposes.

Within an athletic organization a predefined roster of athletes may be provided access to a network of beverage dispensers associated with the athletic organization. Because of the limited number of athletes on even the most robust team rosters, user profiles for each of the athletes may be actively synchronized on the beverage dispensers within the network. Upon a profile of one of the athletes being changed, the updated profile is published to each of the beverage dispensers in the network. By actively synchronizing the profile across the dispensers of the network, changes to the profile may be made between dispensing sessions so that a different beverage may be dispensed each time an athlete uses a dispenser, if desired. Therefore, the beverage dispensed to the athlete may adapt over time to match the performance and preferences of the athlete.

The user profiles include performance parameters and personal parameters. The performance parameters include selections of an amount of one or more functional additives to include in a dispensed beverage. Functional additives include additives that affect an athletic performance of an athlete. The functional additives may include vitamins, minerals, electrolytes such as sodium, potassium, magnesium, and calcium, proteins, carbohydrates, medicines or other functional supplements to be included in a dispensed beverage. The personal parameters include selections of personal preferences for a dispensed beverage, such as flavor, flavor intensity level, level of sweetness, or other non-functional beverage preferences.

The user profiles are centrally maintained on a profile database accessible through a profile server. A user may access and update a profile via an application on a mobile device, a desktop application, a web portal, or the like. Different users are given different levels of access to the profiles maintained on the profile database. For example, each athlete is given access to view their entire profile and make modifications to personal parameters in their profile. In some implementations, athletes are not given access to make modifications to performance parameters in their profile. Likewise, trainers or other training staff of the athletic organization may be given access to view personal parameters of athlete's profiles and access to make modifications to performance parameters of the athletes in the athletic organization. Additionally, external users not affiliated with the athletic organization may be given access to view personal parameters and/or performance parameters of athlete's profiles.

In use, an athlete may address a beverage dispenser in the network of beverage dispensers for the athletic organization and select their profile. For example, the athlete may select their profile from a menu displayed on the beverage dispenser. Upon receiving a selection of the athlete's profile, the beverage dispenser may be configured according to the personal parameters and performance parameters stored in the athlete's profile. The athlete can then dispense a beverage according to the performance and personal parameters in their profile. Upon completion of the dispensing session on the beverage dispenser, a report of the dispensing session may be displayed on an external display. For example, the report may include information about the athlete, their personal parameters selected for the dispensed beverage, an amount of beverage dispensed in the dispensing session, and one or more of the performance parameters of the dispensed beverage. Additional information about the athlete or the athletic organization may be displayed in the report.

Described herein are example systems and methods for profile management in a network of beverage dispensing systems (such as a Coca-Cola® Freestyle®, traditional fountain dispenser, or traditional fountain dispenser with micro-ingredients). For example, a beverage dispensing system (which may include one or more macro-ingredients and one or more micro-ingredients) combines macro-ingredients (such as sweeteners, water, or carbonated water) and micro-ingredients (such as high intensity sweeteners, flavorings, food acids, or additives) to create a finished beverage. Such micro-dosing functionality may increase the dispensing capabilities of the beverage dispensing system to deliver a large variety of beverages adapted to the personal and performance parameters of an athlete.

Generally described, the macro-ingredients may have reconstitution ratios in the range from full strength (no dilution) to about six (6) to one (1) (but generally less than about ten (10) to one (1)). As used herein, the reconstitution ratio refers to the ratio of diluent (e.g., water or carbonated water) to beverage ingredient. Therefore, a macro-ingredient with a 5:1 reconstitution ratio refers to a macro-ingredient that is to be dispensed and mixed with five parts diluent for every part of the macro-ingredient in the finished beverage. Many macro-ingredients may have reconstitution ratios in the range of about 3:1 to 5.5:1, including 4.5:1, 4.75:1, 5:1, 5.25:1, 5.5:1, and 8:1 reconstitution ratios.

The macro-ingredients may include sweeteners such as sugar syrup, HFCS ("High Fructose Corn Syrup"), FIS ("Fully Inverted Sugar"), MIS ("Medium Inverted Sugar"), mid-calorie sweeteners comprised of nutritive and non-nutritive or high intensity sweetener blends, and other such nutritive sweeteners that are difficult to pump and accurately meter at concentrations greater than about 10:1—particularly after having been cooled to standard beverage dispensing temperatures of around 35-45° F. An erythritol sweetener may also be considered a macro-ingredient sweetener when used as the primary sweetener source for a beverage, though typically erythritol will be blended with other sweetener sources and used in solutions with higher reconstitution ratios such that it may be considered a micro-ingredient as described below.

The macro-ingredients may also include traditional BIB ("bag-in-box") flavored syrups (e.g., COCA-COLA bag-in-box syrup) which contain all of a finished beverage's sweetener, flavors, and acids that when dispensed is to be mixed with a diluent source such as plain or carbonated water in ratios of around 3:1 to 6:1 of diluent to the syrup. Other typical macro-ingredients may include concentrated extracts, purees, juice concentrates, dairy products or concentrates, soy concentrates, and rice concentrates.

The macro-ingredient may also include macro-ingredient base products. Such macro-ingredient base products may include the sweetener as well as some common flavorings, acids, and other common components of a plurality of different finished beverages. However, one or more additional beverage ingredients (either micro-ingredients or macro-ingredients as described herein) other than the diluent are to be dispensed and mix with the macro-ingredient base product to produce a particular finished beverage. In other words, the macro-ingredient base product may be dispensed and mixed with a first micro-ingredient non-sweetener flavor component to produce a first finished beverage. The same macro-ingredient base product may be dispensed and mixed with a second micro-ingredient non-sweetener flavor component to produce a second finished beverage.

The macro-ingredients described above may be stored in a conventional bag-in-box container in, at and/or remote from the dispenser. The viscosity of the macro-ingredients may range from about 1 to about 10,000 centipoise and generally over 100 centipoises or so when chilled. Other types of macro-ingredients may be used herein.

The micro-ingredients may have reconstitution ratios ranging from about ten (10) to one (1) and higher. Specifically, many micro-ingredients may have reconstitution ratios in the range of about 20:1, to 50:1, to 100:1, to 300:1, or higher. The viscosities of the micro-ingredients typically range from about one (1) to about six (6) centipoise or so, but may vary from this range. In some instances, the viscosities of the micro-ingredients may be forty (40) centipoise or less. Examples of micro-ingredients include natural or artificial flavors; flavor additives; natural or artificial colors; artificial sweeteners (high potency, nonnutritive, or otherwise); antifoam agents, nonnutritive ingredients, additives for controlling tartness, e.g., citric acid or potassium citrate; functional additives such as vitamins, minerals, electrolytes such as sodium, potassium, magnesium, and calcium, proteins, supplements, herbal extracts, nutraceuticals; and over the counter (or otherwise) medicines such as pseudoephedrine, acetaminophen; and similar types of ingredients. Various acids may be used in micro-ingredients including food acid concentrates such as phosphoric acid, citric acid, malic acid, or any other such common food acids. Various types of alcohols may be used as either macro- or micro-ingredients. The micro-ingredients may be in liquid, gaseous, or powder form (and/or combinations thereof including soluble and suspended ingredients in a variety of media, including water, organic solvents, and oils). Other types of micro-ingredients may be used herein.

Typically, micro-ingredients for a finished beverage product include separately stored non-sweetener beverage component concentrates that constitute the flavor components of the finished beverage. Non-sweetener beverage component concentrates do not act as a primary sweetener source for the finished beverage and do not contain added sweeteners, though some non-sweetener beverage component concentrates may have sweet tasting flavor components or flavor components that are perceived as sweet in them. These non-sweetener beverage component concentrates may include the food acid concentrate and food acid-degradable (or non-acid) concentrate components of the flavor, such as described in commonly owned U.S. patent application Ser. No. 11/276,553, entitled "Methods and Apparatus for Making Compositions Comprising and Acid and Acid Degradable Component and/or Compositions Comprising a Plurality of Selectable Components," which is herein incorporated by reference in its entirety. As noted above, micro-ingredients may have reconstitution ratios ranging from about ten (10) to one (1) and higher, where the micro-ingredients for the separately stored non-sweetener beverage component concentrates that constitute the flavor components of the finished beverage typically have reconstitution ratios ranging from 50:1, 75:1, 100:1, 150:1, 300:1, or higher.

For example, the non-sweetener flavor components of a cola finished beverage may be provided from separately stored first non-sweetener beverage component concentrate and a second non-sweetener beverage component concentrate. The first non-sweetener beverage component concentrate may comprise the food acid concentrate components of the cola finished beverage, such as phosphoric acid. The second non-sweetener beverage component concentrate may comprise the food acid-degradable concentrate components of the cola finished beverage, such as flavor oils that would react with and impact the taste and shelf life of a non-sweetener beverage component concentrate were they to be stored with the phosphoric acid or other food acid concentrate components separately stored in the first non-sweetener component concentrate. While the second non-sweetener beverage component concentrate does not include the food acid concentrate components of the first non-sweetener beverage component concentrate (e.g., phosphoric acid), the second non-sweetener beverage component concentrate may still be a high-acid beverage component solution (e.g., pH less than 4.6).

A finished beverage may have a plurality of non-sweetener concentrate components of the flavor other than the acid concentrate component of the finished beverage. For example, the non-sweetener flavor components of a cherry cola finished beverage may be provided from the separately stored non-sweetener beverage component concentrates described in the above example as well as a cherry non-sweetener component concentrate. The cherry non-sweetener component concentrate may be dispensed in an amount consistent with a recipe for the cherry cola finished beverage. Such a recipe may have more, less, or the same amount of the cherry non-sweetener component concentrate than other recipes for other finished beverages that include the cherry non-sweetener component concentrate. For example, the amount of cherry specified in the recipe for a cherry cola finished beverage may be more than the amount of cherry specified in the recipe for a cherry lemon-lime finished beverage to provide an optimal taste profile for each of the finished beverage versions. Such recipe-based flavor versions of finished beverages are to be contrasted with the addition of flavor additives or flavor shots as described below.

Other typical micro-ingredients for a finished beverage product may include micro-ingredient sweeteners. Micro-ingredient sweeteners may include high intensity sweeteners such as aspartame, Ace-K, steviol glycosides (e.g., Reb A, Reb M), sucralose, saccharin, or combinations thereof. Micro-ingredient sweeteners may also include erythritol when dispensed in combination with one or more other sweetener sources or when using blends of erythritol and one or more high intensity sweeteners as a single sweetener source.

Other typical micro-ingredients for supplementing a finished beverage product may include micro-ingredient flavor additives. Micro-ingredient flavor additives may include additional flavor options that can be added to a base beverage flavor. The micro-ingredient flavor additives may be non-sweetener beverage component concentrates. For example, a base beverage may be a cola flavored beverage, whereas cherry, lime, lemon, orange, and the like may be added to the cola beverage as flavor additives, sometimes referred to as flavor shots. In contrast to recipe-based flavor versions of finished beverages, the amount of micro-ingredient flavor additive added to supplement a finished beverage may be consistent among different finished beverages. For example, the amount of cherry non-sweetener component concentrate included as a flavor additive or flavor shot in a cola finished beverage may be the same as the amount of cherry non-sweetener component concentrate included as a flavor additive or flavor shot in a lemon-lime finished beverage. Additionally, whereas a recipe-based flavor version of a finished beverage is selectable via a single finished beverage selection icon or button (e.g., cherry cola icon/button), a flavor additive or flavor shot is a supplemental selection in addition to the finished beverage selection icon or button (e.g., cola icon/button selection followed by a cherry icon/button selection).

As is generally understood, such beverage selections may be made through a touchscreen user interface or other typical beverage user interface selection mechanism (e.g., buttons) on a beverage dispenser. The selected beverage, including any selected flavor additives, may then be dispensed upon the beverage dispenser receiving a further dispense command through a separate dispense button on the touchscreen user interface or through interaction with a separate pour mechanism such as a pour button (electromechanical, capacitive touch, or otherwise) or pour lever.

In the traditional BIB flavored syrup delivery of a finished beverage, a macro-ingredient flavored syrup that contains all of a finished beverage's sweetener, flavors, and acids is mixed with a diluent source such as plain or carbonated water in ratios of around 3:1 to 6:1 of diluent to the syrup. In contrast, for a micro-ingredient delivery of a finished beverage, the sweetener(s) and the non-sweetener beverage component concentrates of the finished beverage are all separately stored and mixed together about a nozzle when the finished beverage is dispensed. Example nozzles suitable for dispensing of such micro-ingredients include those described in commonly owned U.S. provisional patent application Ser. No. 62/433,886, entitled "Dispensing Nozzle Assembly," PCT patent application Ser. No. PCT/US15/026657, entitled "Common Dispensing Nozzle Assembly," U.S. Pat. No. 7,866,509, entitled "Dispensing Nozzle Assembly," or U.S. Pat. No. 7,578,415, entitled "Dispensing Nozzle Assembly," which are all herein incorporated by reference in their entirety.

In operation, the beverage dispenser may dispense finished beverages from any one or more of the macro-ingredient or micro-ingredient sources described above. For example, similar to the traditional BIB flavored syrup delivery of a finished beverage, a macro-ingredient flavored syrup may be dispensed with a diluent source such as plain or carbonated water to produce a finished beverage. Additionally, the traditional BIB flavored syrup may be dispensed with the diluent and one or more micro-ingredient flavor additives to increase the variety of beverages offered by the beverage dispenser.

Micro-ingredient-based finished beverages may be dispensed by separately dispensing each of the two or more non-sweetener beverage component concentrates of the finished beverage along with a sweetener and diluent. The sweetener may be a macro-ingredient sweetener and/or a micro-ingredient sweetener and the diluent may be water and/or carbonated water. For example, a micro-ingredient-based cola finished beverage may be dispensed by separately dispensing food acid concentrate components of the cola finished beverage, such as phosphoric acid, food acid-degradable concentrate components of the cola finished beverage, such as flavor oils, macro-ingredient sweetener, such as HFCS, and carbonated water. In another example, a micro-ingredient-based diet-cola finished beverage may be dispensed by separately dispensing food acid concentrate components of the diet-cola finished beverage, food acid-degradable concentrate components of the diet-cola finished beverage, micro-ingredient sweetener, such as aspartame or an aspartame blend, and carbonated water. As a further example, a mid-calorie micro-ingredient-based cola finished beverage may be dispensed by separately dispensing food acid concentrate components of the mid-calorie cola finished beverage, food acid-degradable concentrate components of the mid-calorie cola finished beverage, a reduced amount of a macro-ingredient sweetener, a reduced amount of a micro-ingredient sweetener, and carbonated water. By reduced amount of macro-ingredient and micro-ingredient sweeteners, it is meant to be in comparison with the amount of macro-ingredient or micro-ingredient sweetener used in the cola finished beverage and diet-cola finished beverage. As a final example, a supplemental flavored micro-ingredient-based beverage, such as a cherry cola beverage or a cola beverage with an orange flavor shot, may be dispensed by separately dispensing a food acid concentrate components of the flavored cola finished beverage, food acid-degradable concentrate components of the flavored cola finished beverage, one or more non-sweetener micro-ingredient flavor additives (dispensed as either as a recipe-based flavor version of a finished beverage or a flavor shot), a sweetener (macro-ingredient sweetener, micro-ingredient sweetener, or combinations thereof), and carbonated water. While the above examples are provided for carbonated beverages, they apply to still beverages as well by substituting carbonated water with plain water.

The various ingredients may be dispensed by the beverage dispenser in a continuous pour mode where the appropriate ingredients in the appropriate proportions (e.g., in a predetermined ratio) for a given flow rate of the beverage being dispensed. In other words, as opposed to a conventional batch operation where a predetermined amount of ingredients is combined, the beverage dispenser provides for continuous mixing and flows in the correct ratio of ingredients for a pour of any volume. This continuous mix and flow method can also be applied to the dispensing of a particular size beverage selected by the selection of a beverage size button by setting a predetermined dispensing time for each size of beverage.

FIG. 1 illustrates an exemplary block diagram of a beverage dispenser network 100 according to various embodiments of the disclosure. The beverage dispenser network 100 includes one or more mobile dispensers 102 and one or more fixed dispensers 104. The mobile dispensers 102 are installed on support carts for supplying power, water, and any other support features for operating the mobile dispensers 102. For example, the support carts may store and supply one or more macro-ingredients in addition to water, such as a sweetener, carbohydrate, or protein source. Additionally, the support carts may supply carbon dioxide or other ingredients to the mobile dispensers 102. In various embodiments of the disclosure, the mobile dispensers 102 are self-contained dispensing units that store all required beverage ingredients and carbon dioxide within the dispenser housing and only receive water and power external from the dispenser (e.g., from the support cart).

The fixed dispensers 104 are installed at a fixed location 106 accessible to athletes of an athletic organization. For example, the fixed location 106 in which the fixed dispensers 104 may be installed may be a training facility for the athletes. While only one fixed location 106 is shown in FIG. 1, multiple such fixed locations may have fixed dispensers 104 installed therein. For example, multiple training facilities may be accessible to the athletes. Likewise, a home stadium for athletic competitions may include one or more fixed dispensers 104 installed along the sidelines, in a dugout, in a locker room, or other such locations in the home stadium.

One or more of the mobile dispensers 102 may also be used at the training facilities or home stadium. Additionally, one or more of the mobile dispensers 102 may travel with the athletic organization for away games or other events away from their standard training and home stadium facilities.

Each of the dispensers in the beverage dispenser network 100 are identified as such by being associated with a customer number of the athletic organization. In other words, the beverage dispenser network 100 is composed of dispensers associated with the customer number. Each of the dispensers also have a unique identifier that uniquely identifies each of the dispensers in the beverage dispenser network 100. A server 108, or other remote computer system and/or database, maintains at least one table that associates the customer number with each of the unique identifiers of the dispensers in the beverage dispenser network 100. In other words, the server 108 maintains an association between the customer number of the athletic organization and unique identifiers for each of the dispensers in the beverage dispenser network 100 of the athletic organization.

The server 108 is in communication with a profile database 110. The profile database 110 is a centralized profile database for the dispensers in the beverage dispenser network 100. The profile database 110 maintains user profiles for each of the athletes or other users in the athletic organization. The profiles may also include the customer number of the athletic organization. Therefore, the customer number of the athletic organization associates profiles in the profile database 110 with the dispensers in the beverage dispenser network.

Each of the dispensers in the beverage dispenser network 100 is in communication with the server 108 via a network 118, such as the Internet, via one or more communication links. For example, the dispensers in the beverage dispenser network 100 may use one or more wired or wireless communication links to connect to the network 118 and communicate with the server 108. Based on the associations established through the customer number of the athletic organization, the server 108 is configured to download and synchronize the user profiles of the athletic organization maintained in the profile database 110 to all of the dispensers in the beverage dispenser network 100 for the athletic organization. Therefore, each dispenser in the beverage dispenser network 100 maintains an up-to-date local copy of the user profiles associated with the customer number stored in the profile database 110.

Each of the user profiles include performance parameters and personal parameters. The performance parameters include selections of an amount of one or more functional additives to include in a dispensed beverage. Functional additives include additives that affect an athletic performance of an athlete. The functional additives may include vitamins, minerals, electrolytes such as sodium, potassium, magnesium, and calcium, proteins, carbohydrates, medicines or other functional supplements to be included in a dispensed beverage. Other functional additives may be used. The personal parameters include selections of personal preferences for a dispensed beverage, such as flavor, flavor intensity level, level of sweetness, or other non-functional beverage preferences. More or fewer personal parameters may be used.

In some implementations, a user profile may have multiple sets of personal parameters specifying different combinations of a user's favorite parameter settings. For example, a user profile may have a first set of personal parameters with a first flavor, a first flavor intensity level, and a first level of sweetness. The user profile may also have a second set of personal parameters with a second flavor, a second flavor intensity level, and second level of sweetness. At least one of the second flavor, the second flavor intensity level, or the second level of sweetness is different than the first flavor, the first flavor intensity level, or the first level of sweetness.

Upon a profile being downloaded to a dispenser in the network 100 and selected by a user, the dispenser is automatically configured to dispense a beverage based on the performance and personal parameters of the selected profile. In use, the dispenser is configured to display a list of user profiles synchronized to the dispenser. The dispenser is configured to receive a selection of one of the user profiles in the list. If more than one set of personal parameters is included in the user profile, the dispenser further receives a selection of the desired set of personal parameters prior to configuring the dispenser to dispense a beverage based on the selected set of personal parameters and the performance parameters of the selected user profile. If only one set of personal parameters is included in the user profile, the dispenser is automatically configured based on the personal and performance parameters of the selected user profile.

Different users can access and update different portions of the user profiles maintained on the profile database 110. End users include individuals with a profile stored in the profile database 110 who are intended to consume a beverage dispensed from the dispenser, such as an athlete. End users may use a mobile device 112a or a mobile device 112b, such as a cell phone or other such mobile computing device, to access and modify their user profiles stored in the profile database 110. For example, a first end user may use a mobile application or a web browser on the mobile device 112a to access the server 108 and modify a first user profile stored in the profile database 110. The first end user is provided access to modify one or more of the personal parameters of the first user profile or add an additional set of personal parameters to the first user profile. The first end user may also be provided access to view the performance parameters of the first user profile, but not provided access to modify any of the performance parameters. In some implementations, the first end user may also be provided with access to modify one or more of the performance parameters. The first end user is not provided with access to make changes to any of the other user profiles stored in the profile database 110.

Administrative users include individuals with access to modify multiple profiles stored in the profile database 110 who are responsible for maintaining the performance parameters of end users, such as athletic trainers. Administrative users may use an administrative console 114a or 114b, such as a desktop, laptop, cell phone, or other computing device, to access and modify user profiles stored in the profile database 110.

For example, a first administrative user may use an application or a web browser on the administrative console 114a to access the server 108 and modify any of a first set of user profiles stored in the profile database 110. The first set of user profiles all have the same customer number and are associated with the same athletic organization. The first administrative user is provided access to modify one or more of the performance parameters of any of the first set of user profiles. Different performance parameters may be set for different profiles in the first set of user profiles. The first administrative user may also be provided access to view the personal parameters of the first set of user profiles, but not provided access to modify any of the personal parameters. In some implementations, the first administrative user may also be provided with access to modify one or more of the personal parameters of the first set of user profiles. By providing access to modify the performance parameters of the first set of user profiles, the first administrative user is able to continuously modify the functional additives provided to end users in dispensed beverages to achieve desired athletic performance.

Upon completion of a dispensing operation on any of the dispensers in the beverage dispenser network 100, a report of the dispensing session may be displayed on an external display 116. For example, the report may include information about the athlete, their personal parameters selected for the dispensed beverage, an amount of beverage dispensed in the dispensing session, and one or more of the performance parameters of the dispensed beverage. Additional information about the athlete or the athletic organization may be displayed in the report.

In some implementations, the dispensers in the beverage dispenser network 100 are configured to generate a dispensing session message upon completion of a dispensing session. The dispensing session message may include a user profile identifier associated with the dispensing session, identifiers of personal and performance parameters used to dispense a beverage in the dispensing session (e.g., one or more beverage ingredient identifiers), and an amount of the beverage and/or amount of one or more of the beverage ingredients dispensed in the dispensing session. The dispensing session message may be sent to the server 108 or another external device (not shown), which in turn obtains additional information for inclusion in the report to be displayed on the external display 116. For example, based on the user profile identifier received in the dispensing session message, the server 108 or other external device may obtain the user profile from the profile database 110 to obtain additional information about an athlete and one or more of the parameters in the user profile.

While described above as a single beverage dispenser network associated with a customer number, the server 108 and profile database 110 may support multiple such beverage dispenser networks.

Figure 2:
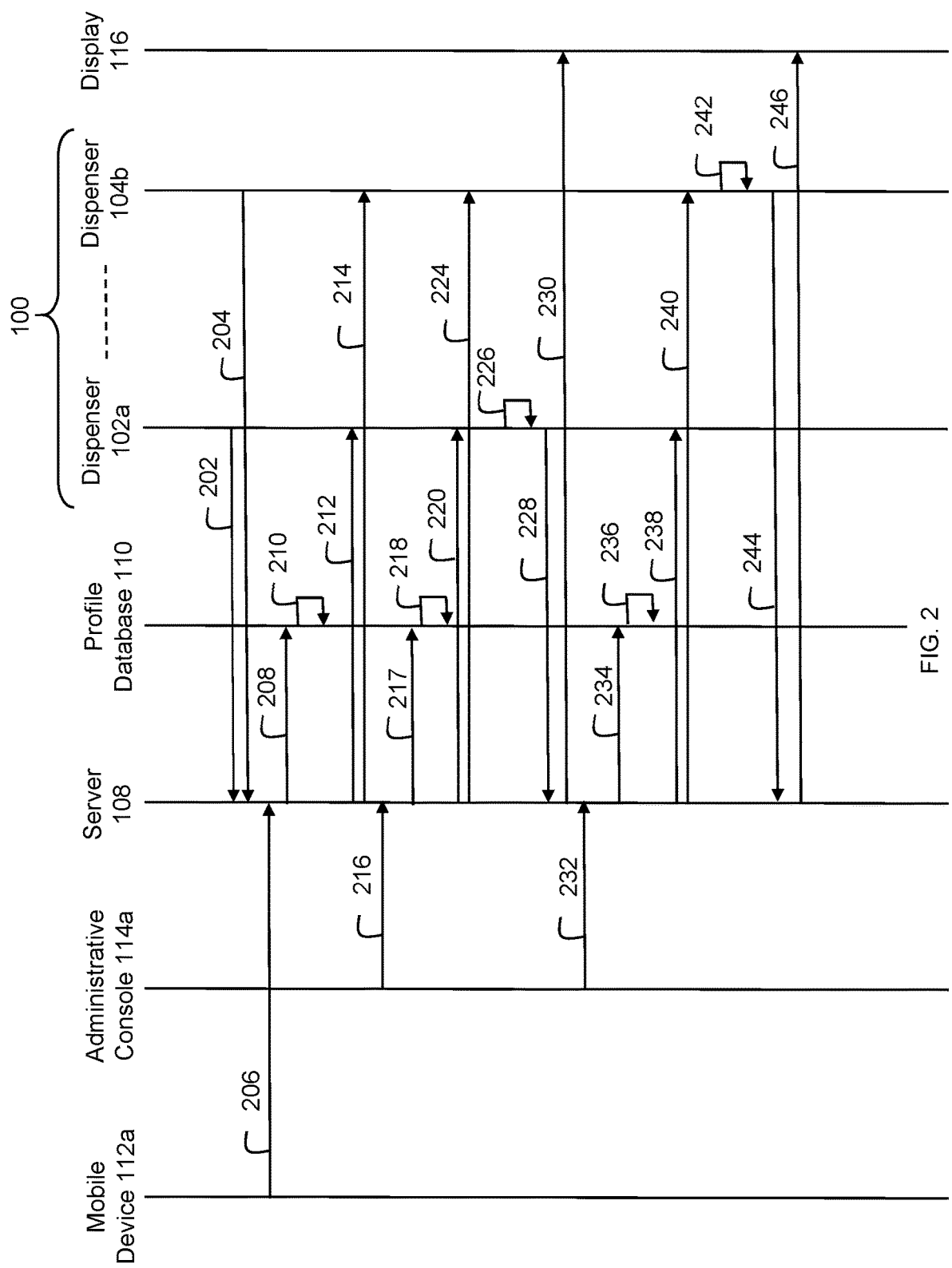
FIG. 2 illustrates a sequence diagram for editing and synchronizing profiles across beverage dispensers of the beverage dispenser network according to various embodiments of the disclosure.

FIG. 2 illustrates a sequence diagram for editing and synchronizing profiles across beverage dispensers of the beverage dispenser network according to various embodiments of the disclosure. At 202 and 204, the dispensers 102a and 104b of the beverage dispenser network 100 subscribe to profile update events published by the server 108. While described herein as a publish and subscribe communication sequence between the dispensers of the beverage dispenser network and the server 108, other messaging protocols for delivering the profile update events from the server 108 to a dispenser may be used. For example, the dispensers of the beverage dispenser network 100 may request updated profiles from the server 108 upon initiating each new dispensing event to download any updates to user profiles. Likewise, the server 108 may communicate the profile update events in a push communication to the dispenser of the beverage dispenser network 100. Other variations and alternatives in the form of communication are contemplated by this disclosure.

At 206, a mobile device 112a of a first end user logs into the server 108 and submits a request to set or modify one or more personal parameters of a first user profile of the first end user. At 208, the server 108 issues a write command to the profile database 110 to update the first user profile stored therein based on the request from the mobile device 112a. At 210, the profile database 110 is updated based on the write command from the server 108.

In response to a successful write operation on the profile database 110, the server 108 publishes a profile update event to the dispensers in the beverage dispenser network 100, such as dispensers 102a and 104b at 212 and 214. For example, the server 108 determines a customer number associated with the first user profile and identifies the dispensers in the beverage dispenser network 100 associated with the customer number. The profile update event is then published to the identified dispensers in the beverage dispenser network 100 based on the customer number. Therefore, each dispenser in the beverage dispenser network 100 maintains an up-to-date local copy of the user profiles associated with the customer number stored in the profile database 110. The profile update event may include the updated first user profile or an indication that an updated version of the first user profile is available to download by the dispensers in the beverage dispenser network 100.

At 216, an administrative console 114a of a first administrative user logs into the server 108 and submits a request to set or modify one or more performance parameters of the first user profile of the first end user. At 217, the server 108 issues a write command to the profile database 110 to update the first user profile stored therein based on the request from the administrative console 114a. At 218, the profile database 110 is updated based on the write command from the server 108.

In response to a successful write operation on the profile database 110, the server 108 publishes a second profile update event to the dispensers in the beverage dispenser network 100. For example, similar to 212 and 214, the server 108 publishes the second profile update to the dispensers 102a and 104b at 220 and 224.

At 226, the first end user addresses the dispenser 102a and navigates to a menu of stored user profiles on the dispenser 102a. For example, the dispenser 102a may receive one or more selections from the first end user through a touch screen display or other user interface device and display a list of user profiles stored thereon. For example, the dispenser 102a displays a list of user profiles of end user in the beverage dispenser network 100 and receives a selection of the first user profile. Upon receiving the selection of the first user profile, the dispenser 102a is configured to dispense a beverage based on the personal and performance parameters in the first user interface, including the updated personal parameters specified at 206 and the updated performance parameters specified at 216. The dispenser 102a conducts a dispensing operation to dispense a beverage based on the personal and performance parameters in the first user interface.

At 228, the dispenser 102a generates a dispensing session message that identifies the selected first user profile, one or more of the personal and/or performance parameters, and an amount or ratio of one or more beverage ingredients and/or an amount of the beverage dispensed in the dispensing session at 226. The dispenser 102a delivers the dispensing session message to the server 108 or another external device (not shown), which in turn generates a report for display on the external display 116 at 230. For example, the report may include information about the first end user (e.g., an athlete), their personal parameters selected for the dispensed beverage, an amount of beverage dispensed in the dispensing session, and one or more of the performance parameters of the dispensed beverage. Elements of the report may be displayed sequentially or simultaneously on the external display 116. Additional information about the athlete or the athletic organization may be displayed in the report.

At 232, the administrative console 114a of a first administrative user logs into the server 108 and submits a second request to set or modify one or more performance parameters of the first user profile of the first end user based on the performance and environmental conditions of the athlete. At 234, the server 108 issues a second write command to the profile database 110 to update the first user profile stored therein based on the second request from the administrative console 114a. At 236, the profile database 110 is updated based on the second write command from the server 108.

In response to a successful write operation on the profile database 110, the server 108 publishes a third profile update event to the dispensers in the beverage dispenser network 100. For example, similar to 212 and 214 above, the server 108 publishes the third profile update to the dispensers 102a and 104b at 238 and 240.

Similar to 226, at 242, the first end user addresses the dispenser 104b and navigates to a menu of stored user profiles on the dispenser 104b. Because the first user profile is synchronized to all of the dispensers in the beverage dispenser network 100, it does not matter which dispenser the first end user addresses to dispense a beverage. The first end user will still be able to access the most recent updates to their user profile. As above, the dispenser 104b may receive one or more selections from the first end user through a touch screen display or other user interface device and display a list of user profiles stored thereon. For example, the dispenser 104b displays a list of user profiles of end user in the beverage dispenser network 100 and receives a selection of the first user profile. Upon receiving the selection of the first user profile, the dispenser 104b is configured to dispense a beverage based on the personal and performance parameters in the first user interface, including the updated performance parameters specified at 232. The dispenser 104b conducts a dispensing operation to dispense a beverage based on the personal and performance parameters in the first user interface.

At 244, the dispenser 104b generates a dispensing session message that identifies the selected first user profile, one or more of the personal and/or performance parameters, and an amount or ratio of one or more beverage ingredients and/or an amount of the beverage dispensed in the dispensing session at 242. The dispenser 102a delivers the dispensing session message to the server 108 or another external device (not shown), which in turn generates a second report for display on the external display 116 at 246.

While examples discussed above with respect to FIG. 2 are provided from the perspective of the first end user, first administrative user, and first user profile, other variations are readily apparent. For example, the first administrative user may additionally modify other user profiles. Additionally, the first administrative user may also change one or more personal parameters of the first user profile. Other variations and changes in the order of the sequence described above are contemplated by this disclosure.

Figure 3A:
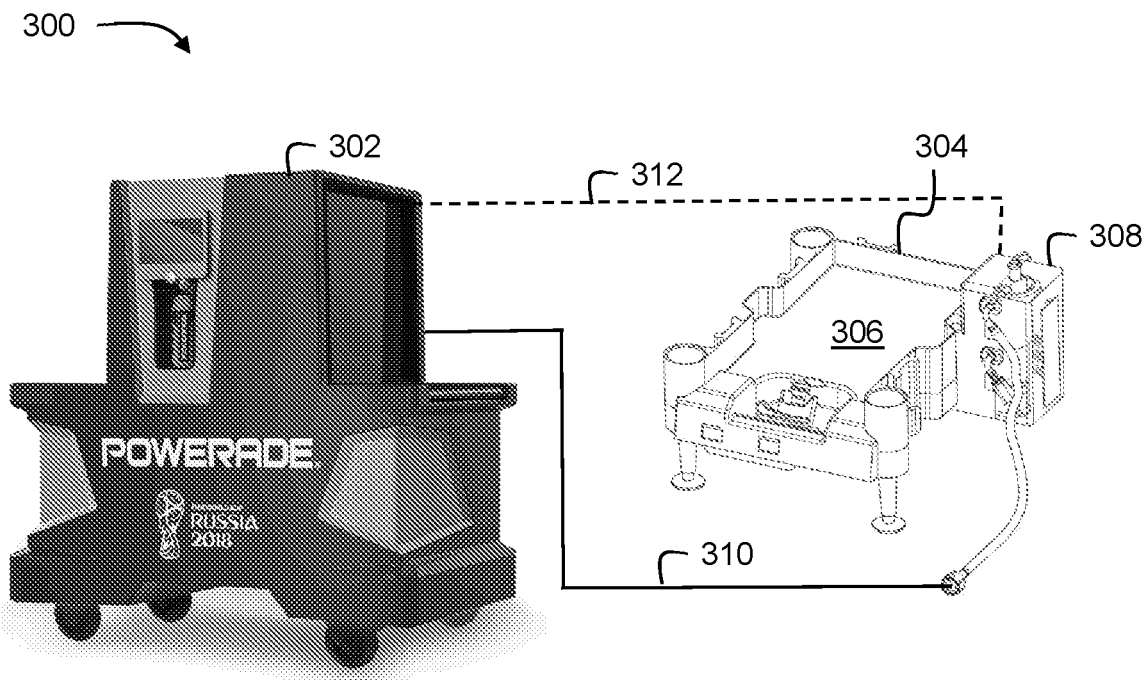
FIGS. 3A-3B illustrate an exemplary beverage dispenser system for facilitating dispensing of additional ingredients suitable for implementing the several embodiments of the disclosure.
Figure 3B:
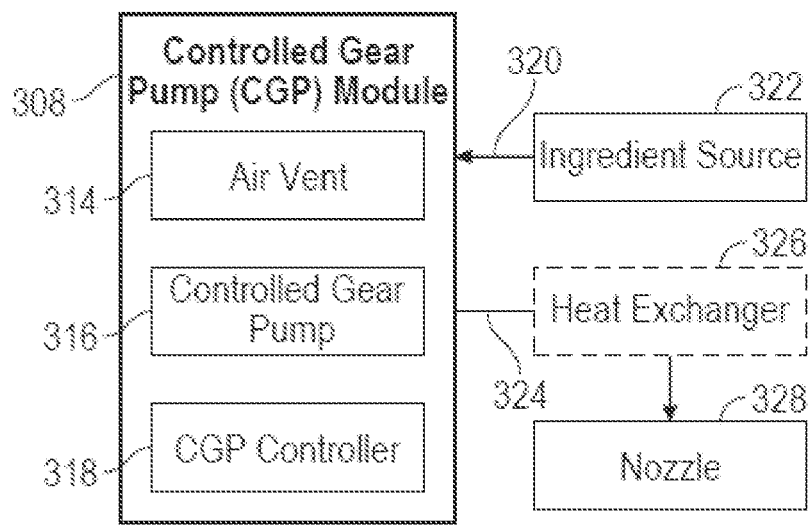

FIGS. 3A-3B illustrate an exemplary beverage dispenser system 300 for facilitating dispensing of additional ingredients suitable for implementing the several embodiments of the disclosure. As shown in FIG. 3A, the beverage dispenser system 300 includes a beverage dispenser 302 and an ingredient tray assembly 304. The beverage dispenser 302 may be one or more of the mobile dispensers 102 or fixed dispensers 104, described above. The beverage dispenser 302 includes an ingredient compartment, such as the ingredient matrix discussed in reference to FIG. 5 below, for storing one or more ingredient packages containing beverage ingredients in fluid communication with a nozzle of the beverage dispenser 302. The ingredient packages stored in the ingredient compartment may be micro-ingredient cartridges with about 42 fluid ounces of a beverage ingredient, for example. Other volumes of beverage ingredients may be stored in the ingredient matrix.

Some ingredients may be dispensed more frequently or at a higher rate than other ingredients and therefore may need to be more frequently replaced in the beverage dispenser 302. For example, the beverage dispensers 102, 104 may use one or more of the functional additives more than others. Accordingly, the ingredient tray assembly 304 provides for receiving a larger volume ingredient package, such as a 2.5- or 5-gallon bag-in-box. For example, one or more of the electrolytes, such as sodium, potassium, magnesium, or calcium may be dispensed more frequently than other electrolytes or other functional additives dispensed from the dispenser. In an example, sodium is dispensed more frequently. Accordingly, a 2.5- or 5-gallon bag-in-box of a sodium beverage ingredient may be provided to the ingredient tray assembly 304 for dispensing from the beverage dispenser 302.

The ingredient tray assembly 304 includes a tray 306 and a pumping module 308. Examples of the ingredient tray assembly 304 are described in U.S. Ser. No. 15/748,367, entitled "Modular System for Dispensing Additional Ingredients", filed on Jan. 29, 2018, the entirety of which is hereby incorporated by reference. The tray 306 is sized to receive a larger volume ingredient package, such as a 2.5- or 5-gallon bag-in-box. Other volumes of ingredient packages are contemplated by this disclosure. The pumping module 308 is configured to be fluidically connected to an ingredient package received in the tray 306. Additionally, the pumping module 308 is configured to be fluidically connected to the beverage dispenser 302, such as via a beverage ingredient supply line 310.

In various implementations, the pumping module 308 includes one or a plurality of pumps for supplying a beverage ingredient from the ingredient package received in the tray 306 to the dispenser 302. For example, the pumping module 308 may include a plurality of micro-ingredient pumps, such as a piston pump, ceramic pump, or other positive displacement pump suitable for pumping micro-ingredients, configured to supply beverage ingredient to a manifold for deliver to the beverage dispense through a common supply line. In another example, the pumping module 308 may include a single controlled gear pump, as described in more detail below. Other variations in the type and number of pumps are contemplated by this disclosure.

The ingredient tray assembly 304 is electrically connected for communication with a controller of the beverage dispenser 302 via an electrical line 312, such as a CAN or Ethernet cable. The ingredient tray assembly 304 may receive commands for starting, stopping, or varying a flow rate of beverage ingredients supplied by the pumping module 308. Additionally, the ingredient tray assembly 304 may communicate one or more messages to the beverage dispenser 302 regarding a volume of beverage ingredient remaining or a sold-out status of a currently install ingredient package. Other communications between the ingredient tray assembly 304 and the beverage dispenser are contemplated by this disclosure. Alternatively, the beverage dispenser 302 and the ingredient tray assembly 304 may communicate via wireless communication.

Accordingly, the ingredient tray assembly 304 provides for supplying a 2.5- or 5-gallon bag-in-box of an electrolyte, such as sodium to the beverage dispenser 302 so as to reduce the frequency of beverage ingredient package change-over at the beverage dispenser 302 for more frequently dispensed beverage ingredients.

Additionally, it may be desirable to supply one or more functional additives that may not be able to be dispensed via the beverage dispenser 302. For example, a functional additive may have a particulate size or viscosity that is not able to be dispensed from a pump in the beverage dispenser 302, such as a micro-ingredient pump. As an example, some proteins or carbohydrates may be difficult to be dispensed or otherwise clog a pump on the beverage dispenser 302. Accordingly, the pumping module 308 may provide a pump that is suitable for dispensing such ingredients, such as a controlled gear pump.

In an example, a functional additive supplied by the ingredient tray assembly 304 may be a shelf-stable, non-refrigerated protein, such as whey or pea protein, maintained in a suspended solution. In various implementations, the ingredient tray assembly 304 may include an agitator for periodically mixing a beverage ingredient maintained in the ingredient tray 306.

As shown in FIG. 3B, the pumping module 308 may be a controlled gear pump (CGP) module. The CGP module 308 may comprise an air vent 314 and controlled gear pump 316 along with various valves (not shown). An embodiment of the operation and structure of air vent 314, controlled gear pump 316, and associated valves are described in PCT Patent Application Serial No. PCT/US15/028559, entitled Vacuum Side Air Vent, filed on Apr. 30, 2015, the entirety of which is hereby incorporated by reference. In general, the controlled gear pump 316 operates to pump a predetermined volume of a fluid every time the pump is cycled. Air vent 314 operates to separate and vent any air that may be entrained within any fluids from an ingredient package received at the ingredient tray 306. CGP controller 318 provides control signals to air vent 314 and associated valves as well as controlled gear pump 316 based on instructions received via the electrical line 312 from a controller in the beverage dispenser 302. The CGP module 308 includes an inlet 320 for receiving fluid from external ingredient source 322 in the ingredient tray 306 and supplying the fluid to controlled gear pump 316 and air vent 314. The CGP module also includes an outlet 324 for supplying fluid pumped by controlled gear pump 316 to a nozzle 328 on the beverage dispenser 302.

In some embodiments, the fluid from the CGP module 308 may pass through a heat exchanger 326 to moderate the temperature of the fluid as desired before being dispensed from the nozzle 328. For example, the fluid from outlet 324 of one or more of the CGP modules may flow through one or more corresponding fluid circuits in a cold plate, cold water bath, or other such heat exchanger. In some embodiments, one or more CGP modules may be in fluid communication with heat exchanger 326 and one or more other CGP modules may be pumped at ambient temperature to the nozzle 328.

While only one ingredient tray assembly 304 is shown in the examples above, it is contemplated that multiple ingredient tray assemblies may be coupled to the beverage dispenser 302. For example, a first ingredient tray assembly may be configured for supplying a sodium electrolyte beverage additive while a second ingredient tray assembly may be configured for supplying a whey protein beverage additive. Other numbers of ingredient trays and types of ingredients are contemplated by this disclosure. Additional CGP modules may further be added for additional ingredient sources as desired and provided to the nozzle 328 in either temperature controlled or ambient fluid circuits.

Figure 4:
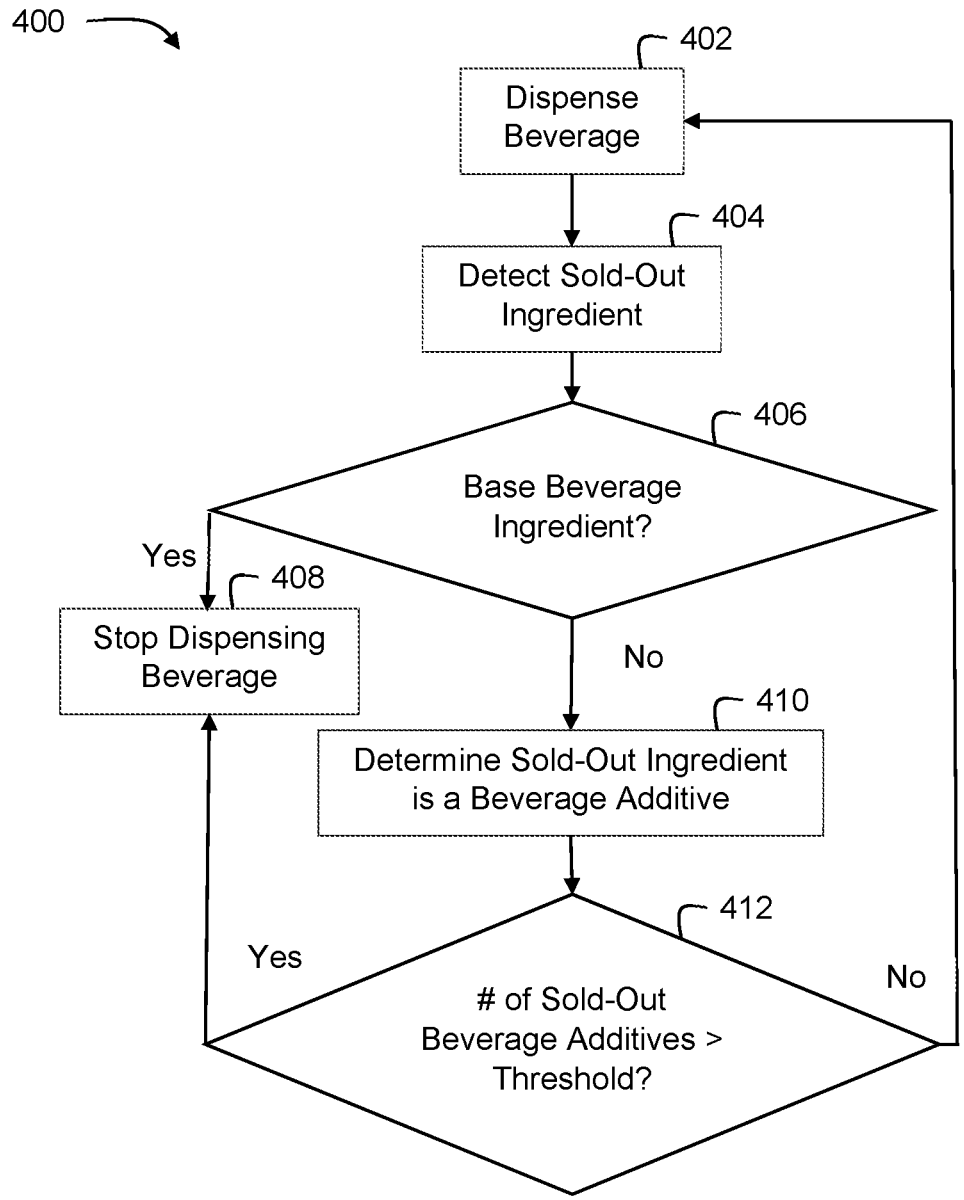
FIG. 4 illustrates a simplified flow diagram for controlling a beverage dispenser as one or more beverage ingredients are depleted.

FIG. 4 illustrates a simplified flow diagram of a control method 400 for controlling a beverage dispenser as one or more beverage additive ingredients are depleted. The control method 400 may be executed by a controller of one or more of the beverage dispensers described throughout this disclosure. As discussed above, beverage additives may include beverage ingredients in addition to a base beverage. Also discussed above, some ingredients may be dispensed more frequently or at a higher rate than other ingredients and therefore may be sold-out (e.g., depleted) or otherwise need to be more frequently replaced in the beverage dispenser 302. Conventionally, a beverage dispenser may discontinue dispensing a beverage if one or more of the ingredients that constitute the beverage are sold-out. The control method 400 provides for continuing to dispense a beverage even when one or more of the beverage additive ingredients are sold-out during the dispense operation.

At 402, the beverage dispenser may initiate dispensing a selected beverage. The selected beverage includes a plurality of ingredients including one or more ingredients for dispensing a base beverage and one or more beverage additive ingredients. For example, the one or more ingredients for dispensing the base beverage may include ingredients that may be adjusted by personal parameters of a user's profile. In another example, the base beverage for a cola beverage may include a food acid concentrate component of a flavored cola finished beverage, food acid-degradable concentrate components of the flavored cola finished beverage, a sweetener, and carbonated water. Following this example, a beverage additive ingredient may include one or more non-sweetener micro-ingredient flavor shots (as opposed to a recipe-based flavor). In a further example, a beverage additive ingredient may include a functional additive that is being dispensed in addition to a base beverage. Other examples of base beverage ingredients and beverage additive ingredients are contemplated by this disclosure.

At 402, the beverage dispenser may detect that an ingredient in the selected beverage is sold-out. The beverage dispenser may detect the sold-out ingredient prior to or during dispensing the selected beverage. At 406, the beverage dispenser determines whether the sold-out beverage ingredient is a base beverage ingredient. If so, the beverage dispenser stops dispensing the beverage at 408. Otherwise, the beverage dispenser determines that the sold-out ingredient is a beverage additive ingredient at 410.

At 412, the beverage dispenser determines whether a number of sold-out beverage additive ingredients exceeds a threshold number of sold-out beverage additive ingredients. If so, the beverage dispenser stops dispensing the beverage at 408. Otherwise, the beverage dispenser continues to dispense the beverage at 402. For example, the beverage dispenser may continue to dispense the beverage if a single beverage additive ingredient in the selected beverage is sold-out, but discontinue dispensing the beverage if more than one beverage additive ingredient in the selected beverage is sold-out. Other numbers of sold-out beverage additive ingredients may be used as the threshold. For example, the beverage dispenser may continue dispensing the selected beverage if 2, 3, 4, or more beverage additive ingredients are sold-out.

While a particular example of the control method 400 is described above, other variations are contemplated by this disclosure. For example, rather than discontinuing dispensing upon a threshold number of beverage additive ingredients are sold-out, other stopping criteria may be used. For example, the beverage dispenser may stop dispensing the selected beverage in response to determining that a particular beverage additive is sold-out. Other examples are contemplated by this disclosure.

Figure 5:
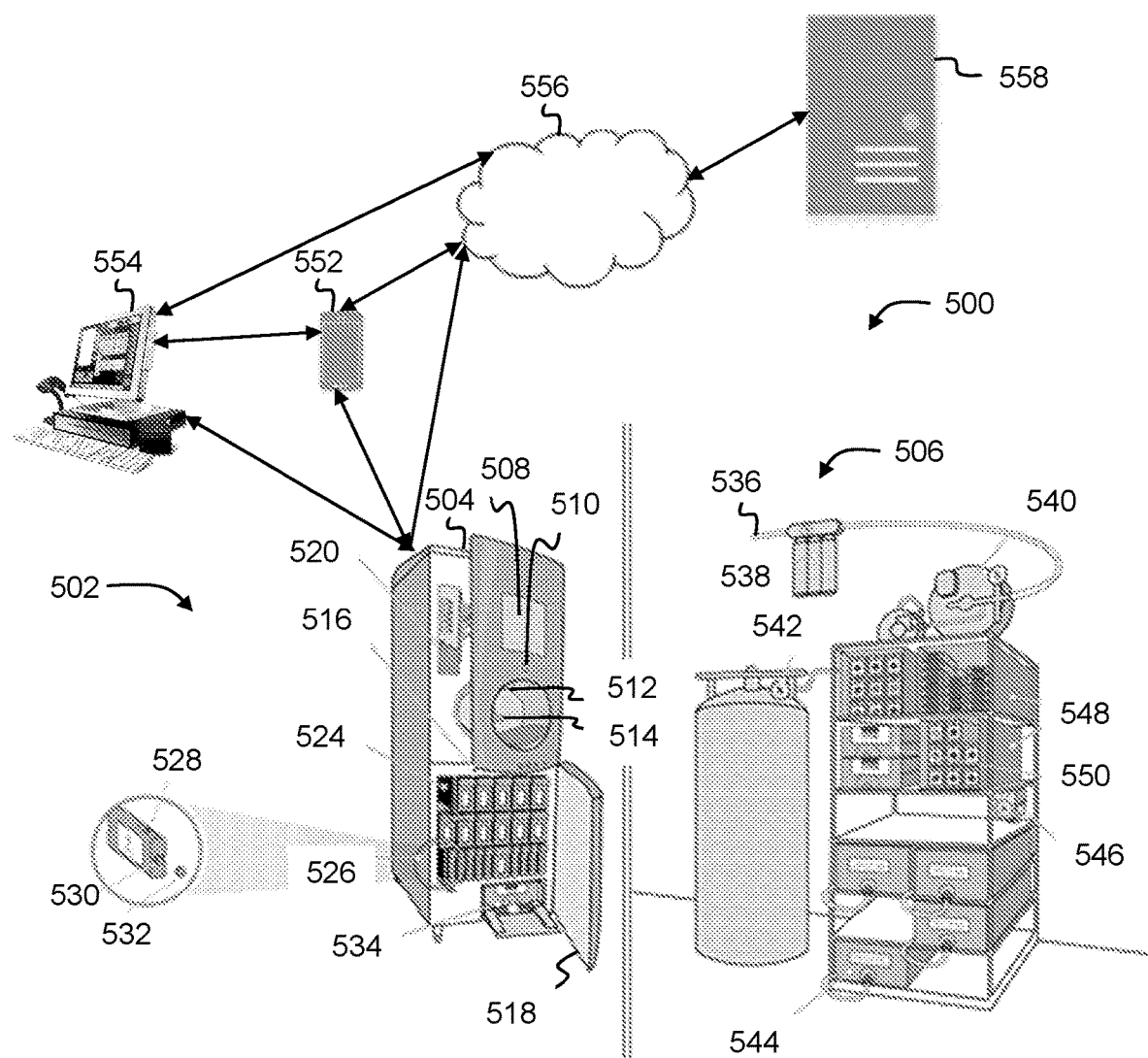
FIG. 5 illustrates an exemplary beverage dispenser system suitable for implementing the several embodiments of the disclosure.

FIG. 5 illustrates an exemplary beverage dispenser system 500 suitable for implementing the several embodiments of the disclosure. As shown, the beverage dispenser system 500 is configured as an ice cooled beverage dispenser. Other configurations of beverage dispensers are contemplated by this disclosure such as a drop-in ice-cooled beverage dispenser, a counter electric beverage dispenser, a remote recirculation beverage dispenser, or any other beverage dispenser configuration.

The beverage dispenser system 500 includes a front room system 502 with a beverage dispenser 504 and a back-room system 506. The beverage dispenser system 500 may be any one of the beverage dispensers 102, 104, 302, described above. The beverage dispenser 504 includes a user interface 508, such as a touchscreen display, to facilitate selection of the beverage to be dispensed. The user interface 508 may employ various screens to facilitate user interactions on the beverage dispenser 504 and/or receive a user profile through interaction with a user's mobile device 552, such as described in commonly owned U.S. patent application Ser. No. 14/485,826, entitled "Product Categorization User Interface for a Dispensing Device," which is herein incorporated by reference in its entirety.

Upon receiving a beverage selection via the user interface 508, a pour button 510 may be activated to dispense the selected beverage from the beverage dispenser 504 via a nozzle 514. For example, the pour button 510 may be an electromechanical button, capacitive touch button, or other button selectable by a user to activate the beverage dispenser 504 to dispense a beverage. While shown as a button, the pour button 510 may alternatively be implemented as a lever or other mechanism for activating the beverage dispenser 504 to dispense a beverage. As shown in FIG. 5, the pour button 510 is separate from the user interface 508. In some implementations, the pour button 510 may be implemented as a selectable icon in the user interface 508.

In some implementations, the beverage dispenser may also include an ice lever 514. Upon being activated, the ice lever 514 may cause the beverage dispenser 504 to dispense ice through an ice chute (not shown). For beverage dispensers that do not have an ice bin, such as counter-electric or remote recirculation beverage dispensers, the ice lever 514 may be omitted.

The beverage dispenser 504 may be secured via a primary door 516 and an ingredient door 518. The primary door 516 and the ingredient door 518 may be secured via one or more locks. In some implementations, the locks are a lock and key. In some implementations, the lock on the ingredient door 518 may be opened via an RFID reader (not shown) reading an authorize ingredient package 528. The primary door 516 may secure electronic components of the beverage dispenser 504 including one or more controllers 520. The ingredient door 518 may secure an ingredient compartment that houses an ingredient matrix 524.

The ingredient matrix 524 includes a plurality of slots 526 for receiving ingredient packages 528. In various implementations, the ingredient packages 528 may be micro-ingredient cartridges. The micro-ingredient cartridges may be single cartridges or double cartridges, such as described in commonly owned U.S. patent application Ser. No. 14/209,684, entitled "Beverage Dispenser Container and Carton," and U.S. patent application Ser. No. 12/494,427, entitled "Container Filling Systems and Methods," which are both herein incorporated by reference in their entirety. As shown in FIG. 5, there are three drawers of ingredients in the ingredient matrix 524. One or more of the drawers may slide back and forth along a rail so as to periodically agitate the ingredients housed on the drawer. Other configurations of the ingredient matrix 524 are possible, such as via one or more static and/or agitated ingredient towers.

Each ingredient package 528 may comprise an RFID tag, a fitment 530, and a fitment seal 532. The fitment seal 532 may be removed prior to installation into the beverage dispenser 504. Upon installation, the fitment 530 may engage with and provide a fluidic communication between a probe (not shown) in the slot 526 and the ingredients contained in the ingredient package 528. The ingredient matrix 524 may also contain one or more large volume micro-ingredient packages 534, such as for one or more micro-ingredient sweetener sources.

The beverage dispenser 504 may also include a carbonator (not shown) for receiving water and carbon dioxide to produce carbonated water. The beverage dispenser 504 may also include one or more heat exchangers (not shown), such as a cold plate, for cooling one or more of the beverage ingredients contained in or received by the beverage dispenser 504. In some implementations, one or more of the micro-ingredients dispensed via the nozzle 512 are not cooled via the heat exchanger or are otherwise maintained at an ambient temperature. Macro-ingredients dispensed via the nozzle 512 are typically cooled via the heat exchanger prior to being dispensed.

The back-room system 506 is typically located in a back room remote from the front room system 502, such as a storage area in a merchant location. The back-room system 506 includes a water source 536 such as a municipal water supply that provides a pressurized source of plain water. The water received via the water source 536 may be filtered or otherwise treated by a water treatment system 538. The treated water may optionally be pressurized to a desired pressure with a water booster 540 and supplied to the beverage dispenser. A carbon dioxide source 542 may supply carbon dioxide to the beverage dispenser 504.

One or more macro-ingredient sources 544 may be located in the back room. The macro-ingredient from each macro-ingredient source 544 may be supplied to the beverage dispenser 504 via a pump 546. The pump 546 may be a controlled gear pump, diaphragm pump, BIB pump, or any other suitable pump for supplying macro-ingredients to the beverage dispenser 504. The back-room system 506 may also include a rack with one or more storage locations 548 for spare micro-ingredients and one or more storage locations 550 for spare macro-ingredients.

The beverage dispenser 504 may include one or more network interfaces for communicating directly with devices in the front room or the back room, communicating with devices in the front room or the back room in a local area network (LAN), or communicating with devices remote from a location with the beverage dispenser system 500 via a wide area network (WAN) connection. For example, the beverage dispenser 504 may include networking devices such as a near field communication (NFC) module, a BLUETOOTH module, a Wi-Fi module, a cellular modem, an Ethernet module, and the like. The beverage dispenser 504 may communicate via a direct communication or via a LAN with a user's mobile device 552 or a point-of-sale (POS) device 554 to receive a beverage selection or user profile of a user for configuring the beverage dispenser 504 to dispense one or more beverages based on the beverage selection or user profile. The user profile may include stored favorite beverages for the user, mixed or blended beverages created or stored by the user in their profile, and/or one or more beverage preferences, such as preferred nutritive level. The beverage dispenser 504 may also communicate via a WAN 556 for communicating with one or more remote servers 558 to receive software updates, content updates, user profiles, or beverage selections made via the remote server 558.

Figure 6:
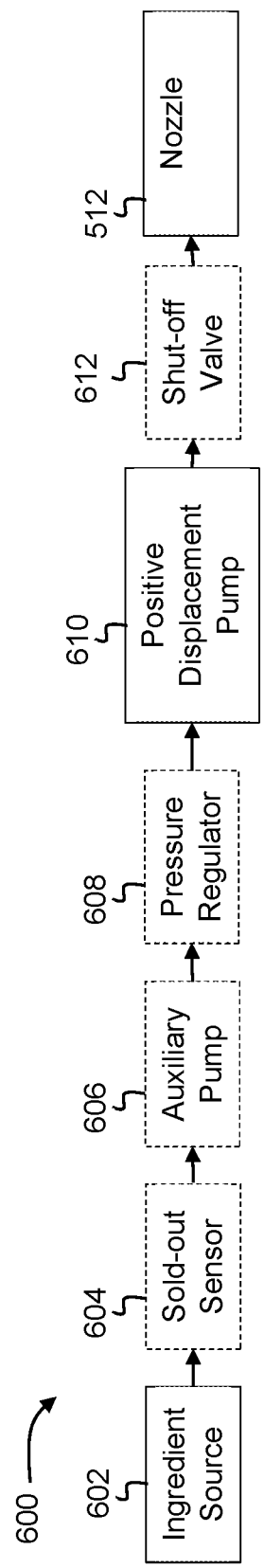
FIG. 6 illustrates an exemplary fluidic circuit with a positive displacement pump suitable for implementing the several embodiments of the disclosure.
Figure 7:
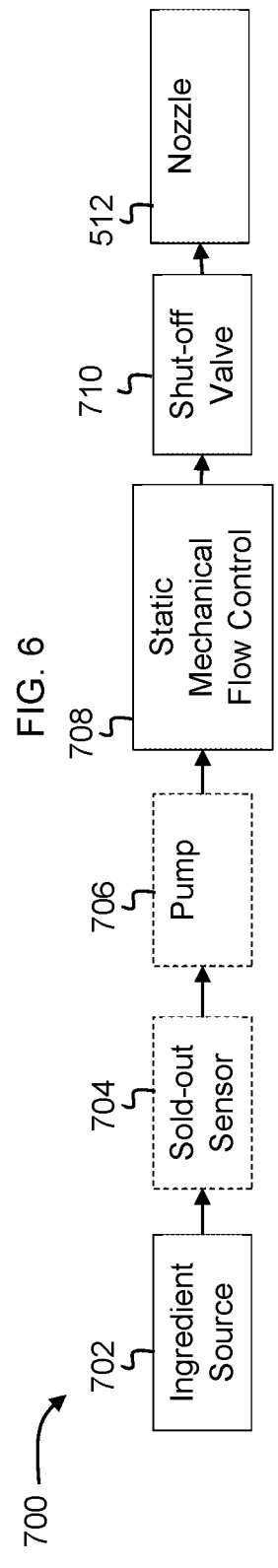
FIG. 7 illustrates an exemplary fluidic circuit with a static mechanical flow control suitable for implementing the several embodiments of the disclosure.
Figure 8:
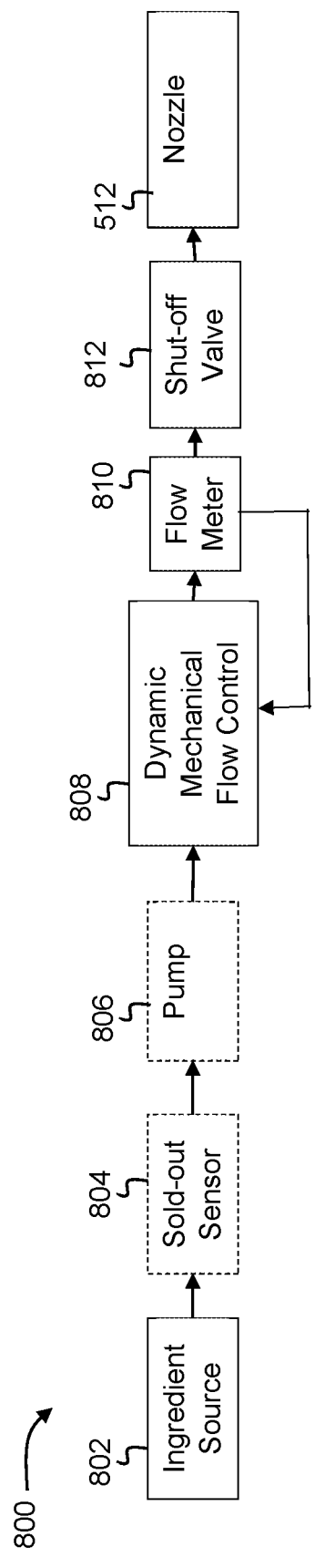
FIG. 8 illustrates an exemplary fluidic circuit with a dynamic mechanical flow control and flow meter suitable for implementing the several embodiments of the disclosure.

FIGS. 6-8 illustrate exemplary fluidic circuits 600-800 with pumping or metering devices from ingredient sources 602, 702, 802 to the nozzle 512 of the beverage dispenser 504. The beverage dispenser 504 may include none, one, or a plurality of the fluidic circuits shown in FIGS. 6-8. For each ingredient source, the beverage dispenser 504 may include one of the fluidic circuits shown in FIGS. 6-8.

FIG. 6 illustrates an exemplary fluidic circuit 600 with a positive displacement pump 610 suitable for implementing the several embodiments of the disclosure. The fluidic circuit 600 provides a fluid path from the ingredient source 602 to the nozzle 512. The ingredient source 602 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The positive displacement pump 610 may meter a predetermined volume or flow rate of ingredient from the ingredient source 602 to the nozzle 512. The positive displacement pump 610 may be a piston pump, controlled gear pump, peristaltic pump, nutating pump, diaphragm pump, or other such positive displacement pump for metering a fixed volume of flow rate of a fluid with each cycle of the pump.

The fluidic circuit 600 may optionally include a sold-out sensor 604 for detecting when the ingredient source 602 is empty. When the ingredient source 602 is remotely located from the beverage dispenser 504, the fluidic circuit 600 may also optionally include an auxiliary pump 606 for providing a pressurized supply of the beverage ingredient to the beverage dispenser 504. Within or immediately adjacent to the beverage dispenser 504, the fluidic circuit 600 may include a pressure regulator 608 such that the inlet of the positive displacement pump 610 receives a lower or zero pressure supply of beverage ingredient. The fluidic circuit 600 may also optionally include a shut-off valve 612 that is configured to remain closed when an ingredient is not being dispensed so as to prevent beverage ingredient from dripping from the nozzle 512.

FIG. 7 illustrates an exemplary fluidic circuit 700 with a static mechanical flow control 708 suitable for implementing the several embodiments of the disclosure. The static mechanical flow control 708 receives a pressurized beverage ingredient from an ingredient source 702 and provides a fixed flow rate of the beverage ingredient to the nozzle 512. The static mechanical flow control 708 may be calibrated with a set screw for configuring the flow rate of the static mechanical flow control 708. A shut-off valve 710 downstream of the static mechanical flow control 708 may be actuated to open and close in order to dispense or prevent dispensing the beverage ingredient from the nozzle 512.

The ingredient source 702 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The ingredient source 702 may also be the municipal water supply 536 or other pressurized ingredient source. When the ingredient source 702 is not pressurized, the fluidic circuit 700 may include a pump 706 for pressurizing the beverage ingredient from the ingredient source 702. The pump 706 may be any pump suitable for pressurizing the beverage ingredient from the ingredient source 702, such as a BIB pump, $CO_2$ driven pump, controlled gear pump, or positive displacement pump. The fluidic circuit 700 may also optionally include a sold-out sensor 704 for detecting when the ingredient source 702 is empty.

FIG. 8 illustrates an exemplary fluidic circuit 800 with a dynamic mechanical flow control 808, a flow meter 810, and a shut-off valve 812 suitable for implementing the several embodiments of the disclosure. The dynamic mechanical flow control 808 receives a pressurized beverage ingredient from an ingredient source 802 and provides an adjustable flow rate of the beverage ingredient to the nozzle 512. The dynamic mechanical flow control 808 may include a variable sized orifice that adjusts to dynamically change the flow rate of the beverage ingredient supplied to the nozzle 512 based on control signals provided by the one or more controllers 520. A flow meter 810 downstream of the dynamic mechanical flow control 808 measures a flow rate of the beverage ingredient being supplied by the dynamic mechanical flow control 808 and provides a feedback loop to the dynamic mechanical flow control 808 for controlling the variable sized orifice. A shut-off valve 812 downstream of the dynamic mechanical flow control 808 may be actuated to open and close in order to dispense or prevent dispensing the beverage ingredient from the nozzle 512.

The ingredient source 802 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The ingredient source 802 may also be the municipal water supply 536 or other pressurized ingredient source. When the ingredient source 802 is not pressurized, the fluidic circuit 800 may include a pump 806 for pressurizing the beverage ingredient from the ingredient source 802. The pump 806 may be any pump suitable for pressurizing the beverage ingredient from the ingredient source 802, such as a BIB pump, $CO_2$ driven pump, controlled gear pump, or positive displacement pump. The fluidic circuit 800 may also optionally include a sold-out sensor 804 for detecting when the ingredient source 802 is empty.

While the components of the fluidic circuits 600-800 are shown in a particular order in FIGS. 6-8, any order of the components described above may be used. For example, the shut-off valve 812 may be upstream of the flow meter 810. Other variations are readily recognizable by those of ordinary skill in the art. Additionally, one or more heat exchangers (not shown) may be used at any location in the fluidic circuits of FIGS. 6-8. The heat exchanger may include an ice bin, water bath, cold plate, or remote recirculation system.

Figure 9:
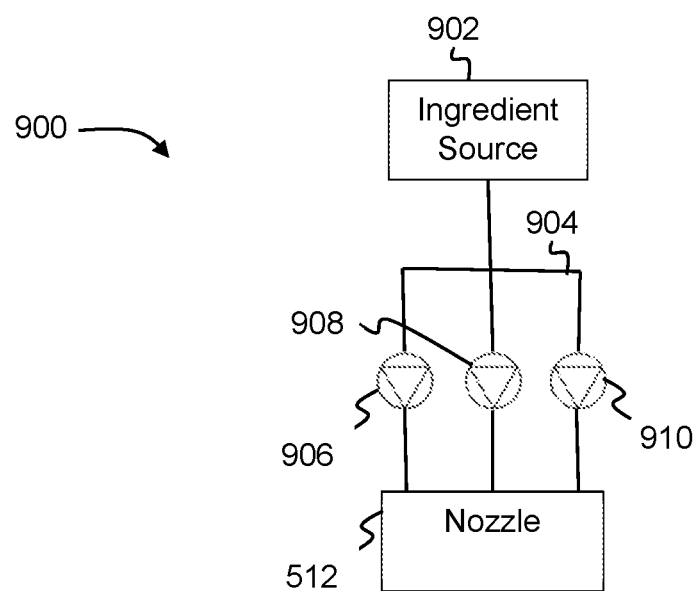
FIG. 9 illustrates an exemplary fluidic circuit with a plurality of independently controlled paths from a single ingredient source suitable for implementing the several embodiments of the disclosure.

FIG. 9 illustrates an exemplary fluidic circuit 900 with a plurality of independently controlled paths from a single ingredient source 902 to the nozzle 512 suitable for implementing the several embodiments of the disclosure. The fluidic circuit 900 includes a manifold 904 for supplying beverage ingredient to each of the independently controlled paths. Each path includes a pumping or metering device 906, 908, 910 for supplying beverage ingredient from the ingredient source 902 to the nozzle 512. The pumping or metering devices 906, 908, 910 may be configured as any of the fluidic circuits 600-800 shown in FIGS. 6-8. By having multiple independent paths from the ingredient source 902 to the nozzle 512, a larger range of flow rates are possible than using any one of the pumping or metering devices 906, 908, 910. For example, for a first flow rate of beverage ingredient from the ingredient source, only one of the pumping or metering devices 906, 908, 910 may be activated. For a second flow rate of the beverage ingredient from the ingredient source, a plurality of the pumping or metering devices 906, 908, 910 may be activated.

Figure 10:
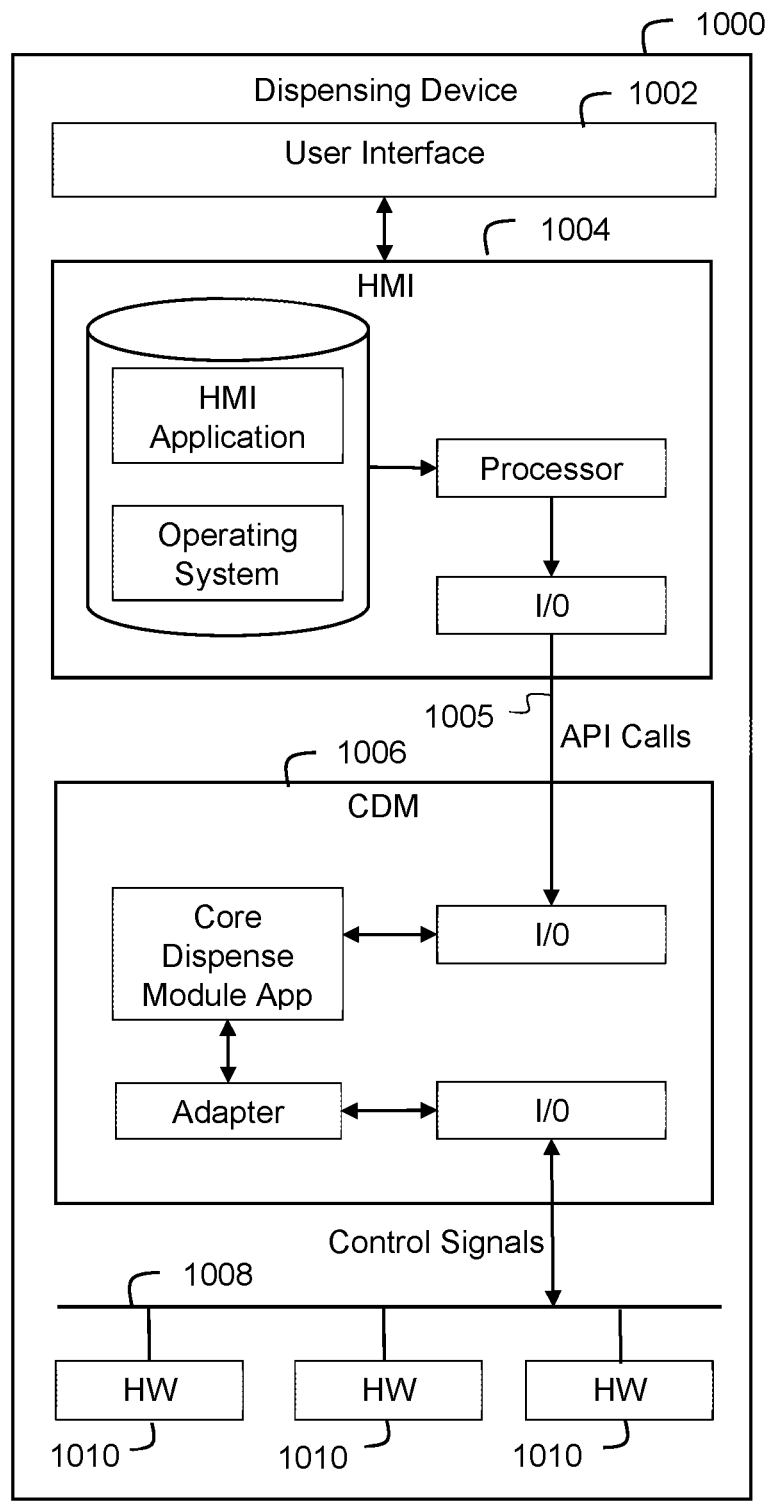
FIG. 10 illustrates an exemplary block diagram of a control architecture for a beverage dispenser suitable for implementing the several embodiments of the disclosure.

FIG. 10 illustrates an exemplary block diagram of a control architecture 1000 that may be used to control the beverage dispenser 504 suitable for implementing the several embodiments of the disclosure. As shown in FIG. 10, control architecture 1000 may comprise a core dispense module (CDM) 1006, a human machine interface (HMI) module 1004, a user interface (UI) 1002, and a machine bus (MBUS) 1005. HMI 1004 may connect to or otherwise interface and communicate with at least one external device (e.g., mobile device 552 or POS 554) being external to beverage dispenser 504. HMI 1004 may also control and update display screens on UI 1002. CDM 1006 may control flows from a plurality of pumps and/or valves 1010 in beverage dispenser 504 according to a recipe to mix and dispense a product (e.g., a beverage) from beverage dispenser 504.

Beverage ingredients (e.g., micro-ingredients, macro-ingredients, and/or diluents) may be combined to dispense various products that may include beverages or blended beverages (i.e., finished beverage products) from beverage dispenser 504. However, beverage dispenser 504 may also be configured to dispense beverage components individually.

An example of control architecture 1000 for beverage dispenser 504 may be described in U.S. Ser. No. 61/987,020, entitled "Dispenser Control Architecture", filed on May 1, 2014, the entirety of which is hereby incorporated by reference. MBUS 1005 may facilitate communication between HMI 1004 and CDM 1006 via one or more API calls. HMI 1004, MBUS 1005, and CDM 1006 may collectively comprise common core components, implemented as hardware or as combination of hardware and software, which may be adapted to provide customized functionality in beverage dispenser 504. Beverage dispenser 504 may further include memory storage and a processor. Examples of UI 1002 may be described in U.S. Ser. No. 61/877,549, entitled "Product Categorization User Interface for a Dispensing Device", filed on Sep. 13, 2013, the entirety of which is hereby incorporated by reference.

UI 1002 may detect what area of a touch screen has been touched by a user (e.g., user 108). In response, UI 1002 may send HMI 1004 data regarding where the touch screen was touched. In response, HMI 1004 may interpret this received data to determine whether to have UI 1002 display a different UI screen or to issue a command to CDM 1006. For example, HMI 1004 may determine that the user touched a portion of the touch screen corresponding to a beverage brand. In response, HMI 1004 may issue a command to CDM 1006 to pour the corresponding beverage brand. In response to receiving the command to pour the corresponding beverage brand, the CDM 1006 in turn issues commands via one or more control buses 1008 to the pumping or metering devices 1010 for the beverage ingredients needed to dispense the beverage brand. Or HMI 1004 may determine that the user touched a portion of the touch screen corresponding to a request for another screen. In response, HMI 1004 may cause UI 1002 to display the requested screen.

In some embodiments, UI 1002 in beverage dispenser 504 may be utilized to select and individually dispense one or more beverages. The beverages may be dispensed as beverage components in a continuous pour operation whereby one or more selected beverage components continue to be dispensed while a pour input is actuated by a user or in a batch pour operation where a predetermined volume of one or more selected beverage components are dispensed (e.g., one ounce at a time). UI 1002 may be addressed via a number of methods to select and dispense beverages. For example, a user may interact with UI 1002 via touch input to navigate one or more menus from which to select and dispense a beverage. As another example, a user may type in a code using an onscreen or physical keyboard (not shown) on beverage dispenser 504 to navigate one or more menus from which to select and dispense a beverage. As a further example, a user may interact with the HMI 1004 via a user interface of an application on the mobile device 552.

UI 1002, which may include a touch screen and a touch screen controller, may be configured to receive various commands from a user (i.e., consumer input) in the form of touch input, generate a graphics output and/or execute one or more operations with beverage dispenser 504 (e.g., via HMI 1004 and/or CDM 1006), in response to receiving the aforementioned commands. A touch screen driver in HMI 1004 may be configured to receive the consumer or customer inputs and generate events (e.g., touch screen events) that may then be communicated through a controller to an operating system of HMI 1004.

Beverage dispenser 504 may be in communication with one or more external device (e.g., mobile device 552 or POS 554). In some embodiments, the communication between beverage dispenser 504 and the external device may be accomplished utilizing any number of communication techniques including, but not limited to, near-field wireless technology such as BLUETOOTH, Wi-Fi and other wireless or wireline communication standards or technologies, via a communication interface.

Figure 11:
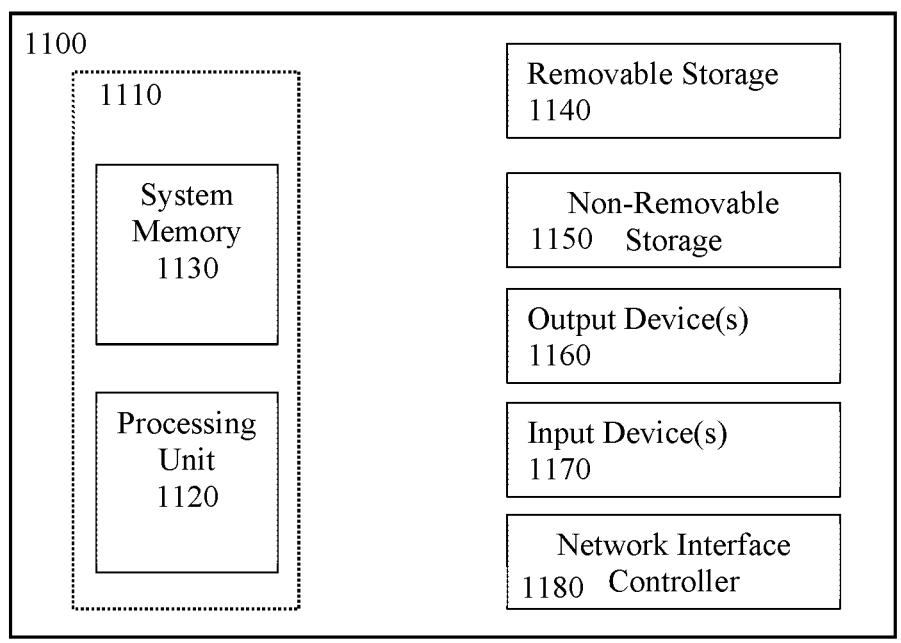
FIG. 11 illustrates an exemplary computer system suitable for implementing the several embodiments of the disclosure.

FIG. 11 illustrates an exemplary computer system 1100 suitable for implementing the several embodiments of the disclosure. For example, one or more components or controller components of the beverage dispenser 504 may be implemented as the computer system 1100. In some implementations, one or both of the HMI 1004 and the CDM 1006 may be implemented as the computer system 1100.

It should be appreciated that the logical operations described herein with respect to the various figures may be implemented (1) as a sequence of computer implemented acts or program modules (i.e., software) running on a computing device (e.g., the computing device described in FIG. 11), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts, and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 11, an example computing device 1100 upon which embodiments of the invention may be implemented is illustrated. For example, each of the dispensers, end user devices, administrator devices, server, profile database, or external display described herein may each be implemented as a computing device, such as computing device 1100. It should be understood that the example computing device 1100 is only one example of a suitable computing environment upon which embodiments of the invention may be implemented. Optionally, the computing device 1100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In some embodiments, the computing device 1100 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In some embodiments, virtualization software may be employed by the computing device 1100 to provide the functionality of a number of servers that is not directly bound to the number of computers in the computing device 1100. For example, virtualization software may provide twenty virtual servers on four physical computers. In some embodiments, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third-party provider. Some cloud computing environments may comprise cloud computing resources owned and operated by the enterprise as well as cloud computing resources hired and/or leased from a third-party provider.

In its most basic configuration, computing device 1100 typically includes at least one processing unit 1120 and system memory 1130. Depending on the exact configuration and type of computing device, system memory 1130 may be volatile (such as random-access memory (RAM)), non-volatile (such as read-only memory (ROM), flash memory, etc.), or some combination of the two. This most basic configuration is illustrated in FIG. 11 by dashed line 1110. The processing unit 1120 may be a standard programmable processor that performs arithmetic and logic operations necessary for operation of the computing device 1100. While only one processing unit 1120 is shown, multiple processors may be present. Thus, while instructions may be discussed as executed by a processor, the instructions may be executed simultaneously, serially, or otherwise executed by one or multiple processors. The computing device 1100 may also include a bus or other communication mechanism for communicating information among various components of the computing device 1100.

Computing device 1100 may have additional features/functionality. For example, computing device 1100 may include additional storage such as removable storage 1140 and non-removable storage 1150 including, but not limited to, magnetic or optical disks or tapes. Computing device 1100 may also contain network connection(s) 1180 that allow the device to communicate with other devices such as over the communication pathways described herein. The network connection(s) 1180 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 1100 may also have input device(s) 1170 such as a keyboard, keypads, switches, dials, mice, track balls, touch screens, voice recognizers, card readers, paper tape readers, or other well-known input devices. Output device(s) 1160 such as a printer, video monitors, liquid crystal displays (LCDs), touch screen displays, displays, speakers, etc. may also be included. The additional devices may be connected to the bus in order to facilitate communication of data among the components of the computing device 1100. All these devices are well known in the art and need not be discussed at length here.

The processing unit 1120 may be configured to execute program code encoded in tangible, computer-readable media. Tangible, computer-readable media refers to any media that is capable of providing data that causes the computing device 1100 (i.e., a machine) to operate in a particular fashion. Various computer-readable media may be utilized to provide instructions to the processing unit 1120 for execution. Example tangible, computer-readable media may include, but is not limited to, volatile media, non-volatile media, removable media, and non-removable media implemented in any method or technology for storage of information such as computer readable instructions, data structures, program modules or other data. System memory 1130, removable storage 1140, and non-removable storage 1150 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 1120 may execute program code stored in the system memory 1130. For example, the bus may carry data to the system memory 1130, from which the processing unit 1120 receives and executes instructions. The data received by the system memory 1130 may optionally be stored on the removable storage 1140 or the non-removable storage 1150 before or after execution by the processing unit 1120.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A beverage dispenser network, comprising:
   a plurality of beverage dispensers, each of the plurality of beverage dispensers configured to locally store a group of user profiles, each of the group of user profiles locally retrievable from a respective one of the plurality of beverage dispensers, wherein each of the group of user profiles comprise a personal parameter for a beverage and a performance parameter for the beverage;
   a profile database configured to centrally store a user profile, wherein the user profile is one of the group of user profiles; and
   a server configured to receive an update to the user profile that changes the personal parameter or the performance parameter of the user profile, wherein the server is configured to send the update to each of the plurality of beverage dispensers in response to the change to the personal parameter or the performance parameter,
   wherein the plurality of beverage dispensers are configured to receive and locally store the user profile with the changed personal or performance parameter from the server in response to the update.

2. The beverage dispenser network of claim 1, wherein the personal parameter is a flavor, flavor intensity level, level of sweetness, or other non-functional additive for a dispensed beverage.

3. The beverage dispenser network of claim 1, wherein the performance parameter is a vitamin, mineral, electrolyte, sodium, potassium, magnesium, calcium, protein, carbohydrate, medicine or other functional additive for a dispensed beverage.

4. The beverage dispenser network of claim 1, wherein the server is configured to permit an administrative user to provide the update to change the performance parameter of the user profile.

5. The beverage dispenser network of claim 4, wherein the server is further configured to permit an end user to provide the update to change the personal parameter of the user profile.

6. The beverage dispenser network of claim 5, wherein the server is further configured to deny the end user to provide the update to change the performance parameter of the user profile.

7. The beverage dispenser network of claim 5, wherein the administrative user is an athletic trainer and the end user is an athlete.

8. The beverage dispenser network of claim 1, further comprising:
   an external display configured to show a report of a dispensing session completed on one of the plurality of beverage dispensers.

9. The beverage dispenser network of claim 1, wherein each of the plurality of beverage dispensers and the user profile are associated with a common customer number.

* * * * *